(12) United States Patent  
Fritsch et al.

(10) Patent No.: US 7,456,028 B2  
(45) Date of Patent: Nov. 25, 2008

(54) ELECTROCHEMICAL METHOD FOR DETECTING WATER BORN PATHOGENS

(75) Inventors: Ingrid Fritsch, Fayetteville, AR (US); Robert Beitle, Jr., Fayetteville, AR (US); Zoraida Aguilar, Cincinnati, OH (US)

(73) Assignee: Board of Trustees of the University of Arkansas, N.A., Little Rock, AR (US)

( * ) Notice: Subject to any disclaimer, the term of this patent is extended or adjusted under 35 U.S.C. 154(b) by 8 days.

(21) Appl. No.: 10/252,342

(22) Filed: Sep. 23, 2002

(65) Prior Publication Data

US 2003/0108922 A1 Jun. 12, 2003

Related U.S. Application Data

(63) Continuation-in-part of application No. 09/978,734, filed on Oct. 15, 2001, now Pat. No. 6,887,714.

(60) Provisional application No. 60/240,691, filed on Oct. 16, 2000.

(51) Int. Cl.  
*G01N 33/543* (2006.01)

(52) U.S. Cl. .................................................. 436/518

(58) Field of Classification Search ................ 436/518; 435/7.1, 7.2, 7.22, 7.32, 7.4, 7.6, 7.72, 7.8, 435/7.9, 7.91, 7.93, 7.94, 7.95, 287.3, 289.1, 435/4–6; 422/50

See application file for complete search history.

(56) References Cited

U.S. PATENT DOCUMENTS

| | | | |
|---|---|---|---|
| 4,779,031 A | 10/1988 | Arends et al. ................ 318/565 |
| 4,891,242 A | 1/1990 | Ito et al. ...................... 427/53.1 |
| 4,945,045 A * | 7/1990 | Forrest et al. .................. 435/25 |
| 4,961,806 A | 10/1990 | Gerrie et al. ................. 156/252 |
| 4,972,470 A | 11/1990 | Farago ............................ 380/3 |
| 5,030,310 A | 7/1991 | Wogoman ................... 156/252 |
| 5,053,920 A | 10/1991 | Staffiere et al. .............. 361/383 |
| 5,066,372 A | 11/1991 | Weetall .................... 205/777.5 |
| 5,159,427 A | 10/1992 | Ogura et al. ................... 357/74 |
| 5,253,156 A | 10/1993 | Sakurai et al. ................. 363/98 |
| 5,290,420 A | 3/1994 | Matson ........................ 204/403 |
| 5,313,150 A | 5/1994 | Arakawa et al. ............ 318/768 |
| 5,344,545 A | 9/1994 | Tsukada et al. ............. 204/415 |
| 5,355,301 A | 10/1994 | Saito et al. ................... 363/147 |
| 5,365,405 A | 11/1994 | Hoenlein et al. ............ 361/766 |
| 5,384,691 A | 1/1995 | Neugebauer et al. ........ 361/794 |
| 5,410,107 A | 4/1995 | Schaper ....................... 174/255 |
| 5,412,558 A | 5/1995 | Sakurai et al. ................. 363/98 |
| 5,432,675 A | 7/1995 | Sorimachi et al. ........... 361/719 |
| 5,434,745 A | 7/1995 | Shokrgozar et al. ......... 361/735 |
| 5,452,182 A | 9/1995 | Eichelberger et al. ....... 361/749 |
| 5,488,542 A | 1/1996 | Ito .............................. 361/793 |
| 5,495,394 A | 2/1996 | Kornfeld et al. ............ 361/764 |
| 5,532,512 A | 7/1996 | Fillion et al. ................ 257/686 |
| 5,544,017 A | 8/1996 | Beilin et al. ................. 361/790 |
| 5,604,383 A | 2/1997 | Matsuzaki ................... 257/778 |
| 5,605,662 A | 2/1997 | Heller et al. ................ 422/68.1 |
| 5,608,192 A | 3/1997 | Moriizumi et al. .......... 174/255 |
| 5,608,617 A | 3/1997 | Morrison et al. ............ 363/147 |
| 5,616,888 A | 4/1997 | McLaughlin et al. ........ 174/260 |
| 5,619,108 A | 4/1997 | Komurasaki et al. ........ 318/140 |
| 5,629,559 A | 5/1997 | Miyahara .................... 257/666 |
| 5,629,574 A | 5/1997 | Cognetti et al. ............... 310/71 |
| 5,634,267 A | 6/1997 | Farnworth et al. ............ 29/840 |
| 5,641,944 A | 6/1997 | Wieloch et al. ............. 174/252 |
| 5,648,227 A * | 7/1997 | Basb.o slashed.ll ........ 435/7.32 |
| 5,698,394 A * | 12/1997 | Duhamel et al. ............... 435/6 |
| 5,846,814 A | 12/1998 | Galla et al. ............... 435/287.2 |
| 5,866,344 A * | 2/1999 | Georgiou .................... 435/7.21 |
| 6,083,763 A * | 7/2000 | Balch ......................... 436/518 |
| 6,391,624 B1 * | 5/2002 | Megerle ................... 435/287.2 |
| 6,436,638 B1 * | 8/2002 | De Leon et al. ................ 435/6 |
| 6,485,983 B1 * | 11/2002 | Lu et al. ..................... 436/514 |
| 6,506,564 B1 * | 1/2003 | Mirkin et al. ................... 435/6 |

OTHER PUBLICATIONS

Hayes et al., "Simultaneous Immunoassay Uisng Electrochemical Detection of Metal Ion Labels", Anal. Chem. 1994, 66, 1860-1865.*  
*Stock Product Catalog 501, Baldor Motors and Drives, Jan. 1, 1997.  
*The Animatics SmartMotor, Animatics Corporation.  
*Industrial electronics, Technology 1998 Analysis & Forecast, IEEE Spectrum, Jan. 1998, p. 73-78.  
*Craig D.T. Bratten, Peter H. Cobbold, Jonathan M. Cooper; Micromachining Sensors for Electrochemical Measurement in Subnanoliter Volumes; *Anal. Chem.*, 1997, vol. 69 No. 2, Jan. 15, 1997, pp. 253-258.

(Continued)

*Primary Examiner*—Ann Y Lam  
(74) *Attorney, Agent, or Firm*—Head, Johnson & Kachigian, P.C.

(57) ABSTRACT

A novel, surface immobilization electrochemical assay allows for rapid, accurate and highly sensitive detection of microorganisms and biological molecules. Known surface immobilization methods are utilized to bind an analyte to a surface. A binding material with a covalently attached electroactive complex generates electrical current in the presence of analyte. An electrode is used to detect the current, that is directly related to the concentration of analyte. The invention is especially suitable for detection of *Cryptospiridium parvum*.

18 Claims, 5 Drawing Sheets

OTHER PUBLICATIONS

*K. Leyendecker, W. Bacher, W. Stark, A. Thommes; New Microelectrodes For the Investigation Of the Electroforming Of Liga Microstructures; *Electrochimica Acta*, 1994, vol. 39, No. 8/9, pp. 1139-1143.

*Osamu Niwa, Masao Morita, Hisao Tabei; Fabrication and characteristics of vertically separated interdigitated aray electrodes; *J. Electroanal. Chem.*, 1989, 267, pp. 291-297.

*Alan M. Bond, Darryl Luscombe, Keith B. Oldham, Cynthia G. Zoski; A Comparison Of the Chronoamperometric Response At Inlaid and Recessed Disc Microelectrodes; *J. Electroanal. Chem.*, 1988, 249, pp. 1-14.

*Thor D. Osborn, Paul Yager; Formation of Planar Solvent-Free Phospholipid Bilayers by Langmuir-Blodgett Transfer of Monolayers to Micromachined Apertures in Silicon; *Langmuir*, 1995, 11, pp. 8-12.

*Rose A. Clark, Paula Beyer Hietpas, Andrew G. Ewing; Electrochemical Analysis in Picoliter Microvials; *Anal. Chem.*, 1997, 69, pp. 259-263.

*K.C. Burgers, K.J. Olejniczak, S.S. Ang, E. Porter; The Use of Multichip Module Technology for Power Electronics Miniaturization and Packaging; Department of Electrical Engineering, University of Arkansas; High Density Electronics Center (HiDEC), University of Arkansas, *Abstract*, 1997, pp. 35-41.

* cited by examiner

```
                            SEQUENCE LISTING

<160> NUMBER OF SEQ ID NOS: 3

<210> SEQ ID NO 1
<211> LENGTH: 33
<212> TYPE: DNA
<213> ORGANISM: Cryptosporidium parvum

<400> SEQUENCE: 1
tatagggaga aggtagaacc accaaccaat aca                              33

<210> SEQ ID NO 2
<211> LENGTH: 42
<212> TYPE: DNA
<213> ORGANISM: Cryptosporidium parvum

<400> SEQUENCE: 2
acatcatgta cagatctctt gtcccgcaac tacgaaggtc tg                    42

<210> SEQ ID NO 3
<211> LENGTH: 44
<212> TYPE: RNA
<213> ORGANISM: Cryptosporidium parvum

<400> SEQUENCE: 3
ggacaagaga ucuguacaug auguuguauu gguugguggu ucua                  44
```

ELECTROCHEMICAL METHOD FOR DETECTING WATER BORN PATHOGENS

CROSS-REFERENCE TO RELATED APPLICATIONS

This application is a continuation-in-part of U.S. patent application Ser. No. 09/978,734, filed Oct. 15, 2001, now U.S. Pat. No. 6,887,714, and claims priority to U.S. provisional application Ser. No. 60/240,691, filed Oct. 16, 2000.

BACKGROUND OF THE INVENTION

1. Field of the Invention

The present invention relates to rapid, accurate and highly sensitive methods for detecting water born pathogens. Specifically, pathogens such as bacteria and/or their heat shock polynucleotides are immobilized on a surface within an assay structure. Electrolabeling molecules are then non-covalently attached to the pathogens. The electrolabeling molecules are then activated so as to generate a current that may be measured. The current generated is quantitativly and directly related to the concentration of the pathogens and accurately correlates thereto. While the present invention is particularly suitable for detection of *Cryptosporidium parvum*, it is also suitable for detecting a wide variety of pathogens, proteins, polynucleotides and a variety of other biological molecules.

2. Prior Art

Combining assays that utilize specific chemical interactions like noncovalent binding, such as hybridization and immunoassays, with electrochemical detection provide for a wide range of uses because highly specific and precise current measurements can be performed with simple instrumentation, using opaque device materials, and in colored and turbid samples minimizing prior pre-treatment procedures. The use of chemical compounds specific to the analyte, such as polynucleotide probes and antibodies, further reduces the need for pre-treatment procedures and facilitates accurate testing of very "dirty" samples.

General immunoassay procedures involve immobilization of the primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate ($PAP_p$). The AP converts $PAP_p$ to p-aminophenol ($PAP_R$, the "R" is intended to distinguish the reduced form from the oxidized form, $PAP_O$, the quinoneimine) which is electrochemically reversible at potentials that do not interfere with reduction of oxygen and water at pH 9.0, where AP exhibits optimum activity. In addition, $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using $PAP_p$ volumes ranging from 20 µl to 360 µL have been reported previously. In capillary immunoassays with electrochemical detection, the lowest detection limit reported thus far is 3000 molecules of mouse IgG using a volume of 70 µL and a 20 min assay time. Those skilled in the art will recognize the above described assay as a sandwich-type immunoassay and will appreciate that this is only one of many immunoassays. Alternatives include competitive binding immunoassays and immunoassays utilizing a more general physisabsorbing material other than a primary antibody.

Immunoassays are only one category of a very wide variety of surface immobilization chemical detection assays. Northern and southern blot assays are well known techniques for detecting specific polynucleotide sequences. They involve surface immobilization of polynucleotides. Surfaces having one or more lipid layers may be used to immobilize and detect compounds having hydrophobic regions. Molecular interactions may also be taken advantage of to develop surface immobilization chemical detection assays. When two molecules are known to bind to one another, one may be covalently attached to a substrate. The substrate is then exposed to a sample such that the other interacting molecule is given an opportunity to bind to the substrate bound molecule. The substrate is then rinsed leaving only bound analyte on the substrate. A number of detecting methods may then be applied to the surface. Detecting methods include using secondary antibodies as described above, detecting the bi-products of an enzymatic reaction characteristic of the analyte, spectroscopy, flourescence, or other methods known to those skilled in the art.

These assays generally require a laboratory setting. A person wishing to analyze a sample with one of the above described assays most usually sends the sample to a laboratory. Even while in a laboratory, many chemical detection assays take a relatively long period of time.

*Cryptosporidium* is a genus of protozoan parasite commonly found in the gastrointestinal tract of vertebrates. There are eight named species of *Cryptosporidium*. *C. parvum* is infectious for 79 species of mammals, including humans, causing acute gastroenteritis. Unlike most parasites, *C. parvum* lacks host specificity among mammals and is able to cross-infect multiple host species.

All infections with *Cryptosporidium* are initiated by ingestion or inhalation of the oocyst. Because the parasite is transmitted in the form of an oocyst, oocysts have evolved to survive in harsh environmental conditions and are unusually resistant to natural stresses and chemical disinfectants. In addition, the presence of an exogenous oocyst encapsulating the protozoan parasite makes the parasite much more resistant to conventional water treatment processes. Measures to prevent or limit the spread of infection concentrate on eliminating or reducing infectious oocysts in the environment. For humans, disinfection procedures are sought to minimize person-to-person transmission and to deal effectively with contamination of water supplies.

Immunological techniques have been used to detect *C. parvum* in environmental specimens. The availability of monoclonal antibodies for specific antigens of *Cryptosporidium* facilitated development of these methods.

Immunofluorescence assays (IFA) are the most common assays used to detect *Cryptosporidium* oocytes in specimens and to detect the presence of a specific antibody. These methods employ fluorescent dyes which are combined with antibodies to make them fluoresce when exposed to ultraviolet light. In a typical IFA assay, water is filtered through a polypropylene cartridge filter or a flat, membrane filter. Both filters yield filtrates that are then subjected to purification before analysis by microscopy. The filtrate is removed from the filter and then centrifuged. Extraneous debris is removed by flotation over a sucrose solution. The supernatant is labeled with a fluorescein conjugated antibody against *Cryptosporidium* and examined by epifluorescence microscopy.

Some commercial immunofluorescent assays and reagents used to detect *Cryptosporidial* oocytes include: (1) HydroFluor Combo, an immunofluorescent assay system based on an oocyst-specific monoclonal antibody (IgM, OW3) (2) Detect IF *Cryptosporidium*, an immunofluorescent assay system based on an oocyte-specific monoclonal antibody (IgM, C1), and (3) Crypto IF Kit, an immunofluorescent assay system based on an oocyst-specific monoclonal antibody.

The disadvantages of immunofluorescence assays include their low recovery efficiency, long processing times, the need for highly trained analysts, high cost, the inability to discriminate viable or virulent strains and cross-reactivity of the probes with similar size and shaped algae. In addition, IFA detection often involves the time consuming and skill intensive step of looking at water sludge under a microscope for oocysts that have been labeled with a fluorescent antibody. It is also often difficult to distinguish oocysts from debris bound non-specifically by the antibodies. The procedure is expensive and often takes days to complete.

Enzyme-linked immunosorbent assays (ELISA) using oocyte-reactive monoclonal antibodies are also used to detect *Cryptosporidium* in contaminated water samples. Two basic ELISA tests have been used in the past for detecting *Cryptosporidium* antigen in samples: (1) the double antibody sandwich technique for the detection of antigens, and (2) the enzyme-linked indirect immunosorbent assay for the detection of antibodies.

In the double antibody sandwich method, antiserum is adsorbed to a well. Test antigen is added and, if complementary, binds to the antibody. An enzyme-linked antibody specific for the test antigen then binds to the antigen, forming a sandwich. The enzyme's substrate is then added, and the reaction produces a visible color change. In the indirect immunosorbent assay, an antigen is adsorbed to a well. Test antiserum is then added, with complementary antibody binding to the antigen. Enzyme-linked anti-human gamma globulin is then added. It binds to the bound antibody. The enzyme's substrate is then added, producing a visible color change.

Detection assays based upon polymerase chain reactions (PCR) have also been used to detect oocysts in clinical or environmental samples. Several DNA and RNA regions of *C. parvum* have been sequenced and have been reported to be assay targets for parasite detection.

Flow cytometry is another method used to detect parasitic contamination of water samples. Flow cytometry techniques can quantify whole oocysts but involves much preparation, and time and require extremely expensive equipment.

Numerous problems are associated with prior art methods of detecting *Cryptosporidium* in water and environmental samples. In addition to those mentioned and the general lack of precise, recitable assays, prior art techniques generally require that samples be transferred to a laboratory or to another remote location for the conduct of the assay. Prior art techniques lack the requisite reliability, speed and sensitivity to accurately detect *Cryptosporidium* in contaminated water samples.

The detection of infectious *C. parvum* oocysts in water and other environmental samples is essential to detecting and treating contaminated water supplies. It is crucial, therefore, that specific, rapid and highly sensitive assays be developed to detect the presence of the parasite accurately and reliably. The known methods of enzyme immunoassays and immunofluorescence do not fulfill these requirements. The source, viability and pathogenicity of oocysts found in water or other environmental samples cannot be reliably determined using prior art methods. There is a need for routine epidemiological surveillance and environmental monitoring that can be conducted on site to provide early detection of the parasite.

It is therefore desirable to provide a method for rapid chemical detection.

It is also desirable to provide a highly sensitive method for detecting low amounts of analyte in a very small amount of sample.

It is also desirable to provide a method for detecting an analyte in a small sample having very high accuracy.

SUMMARY OF THE INVENTION

In the present invention, the shortcomings of the prior art are overcome by a greatly improved electrochemical detection assay. The assay is especially suitable for detection of pathogens and toxins in water supplies, especially *Cryptospiridium parvum*. However, it is also suitable for other pathogens such as, cholera, anthrax, *E. coli* and other pathogens, as well as toxins such as botulinum and multifarious pesticides. The present invention uses known chemical interactions, especially between antibodies and antigens, and polynucleotide probes and polynucleotides. In the past, isotopes and flourescent molecules have been attached to chemical moieties that bind to the chemical or organism to be detected. Flourescence or radioactivity is then used to detect the presence of the analyte. Current detection methods, especially for water-born pathogens and toxins, are time intensive, labor intensive, and wanting in accuracy. By utilizing an electroactive complex, the present invention is fast, sensitive, highly accurate and may be performed on small volumes.

The present invention includes a novel surface immobilization electrochemical assay. The invention combines known surface immobilization and molecular interaction techniques with a novel electrochemical detection method. Any of a number of analyte binding materials are applied to the substrate of an assay structure. A sample to be tested for a specific analyte is then introduced to the assay structure. Any analyte present is then placed under the proper conditions in which it may bind to the analyte binding material. The assay structure is then rinsed to remove all materials other than bound analyte and assay solution. A secondary analyte binding material is then added to the assay structure under conditions allowing it to bind to the bound analyte. The assay structure is then rinsed again such that only the bound analyte and secondary analyte binding material remain on the assay structure. The assay structure is then immersed in either the same or a second assay solution. The secondary analyte binding material has a covalently bound electrochemically active molecule. When activated, the electrochemically active molecule creates a current within the assay structure. After the secondary analyte binding material is given sufficient time to bind to any analyte present, the assay structure is again rinsed to remove any secondary analyte binding material that is not bound analyte. The electrochemically active complex is then activated. If analyte is present, then a current will be created within the assay structure. The strength of the current is directly related to the amount of analyte present.

The enzyme-linked DNA-hybridization assay with electrochemical detection is a new technique for analysis of *C. parvum* that offers improvements over existing EPA detection methods. Using oocysts subjected to heat shock, the assay time from capture of the oocysts to the detection of the electrochemical signal with the macrochip assay takes less than 20 h to complete. It eliminates the time-consuming steps involved in the immunofluorescence detection of the EPA methods such as dye staining, organism fixation, and microscopic quantitative analysis without necessarily eliminating the existing EPA filtration and immunomagnetic separation method. Normal assay time with the existing EPA method could take four days at least from the day the sample has been filtered and the oocysts isolated by immunomagnetic separation whereas, this invention takes less than 20 h to process one sample. The electrochemical signal in our approach is monitored by a potentiostat so it does not require extensive human involvement in the identification and quantification steps. Unlike previously published electrochemical DNA-hybridization assays for *C. parvum*, our system offers many advantages because it separates the biological assembly from the detecting surface. In addition, it is possible to compare signals from the assay of samples before and after heating so that viable oocysts can be detected. It is be possible to achieve proper heating conditions to amplify the mRNA as well. Extended heating can then be used to kill the oocysts and release the mRNA for detection. Specificity for *C. parvum* over other organisms using the assay is extremely high, and is another advantage over the antibody-based EPA methods. The advantages that small volumes and close proximity of electrodes to the modified surfaces involve significantly reduced assay and detection time, as well as dramatic improvement in detection limits.

We have developed a new electrochemical sandwich type enzyme-linked immunosorbant assay for the detection of *C. parvum* in water. The assay shows a faster assay time (~25 h) in comparison with the existing EPA methods, 24 h minimum to two weeks from receipt of sample of *C. parvum* detection. Furthermore, these results show a detection limit of 7 oocysts/L that is about one order of magnitude lower than the existing EPA (Method 1622 and 1623) detection methods (100 oocysts/L). Concentrations within 0.1 to 0.3 oocysts/L in finished water show the possibility of an outbreak to exist. The present EPA goal for a desirable detection limit is 10 oocyst/L based on Method 1622 and 1623. An assay time less than 24 is desirable because over that period, it is too late for the water treatment facilities to prevent and outbreak.

DETAILED DESCRIPTION OF THE PREFERRED EMBODIMENTS

Figure 1:
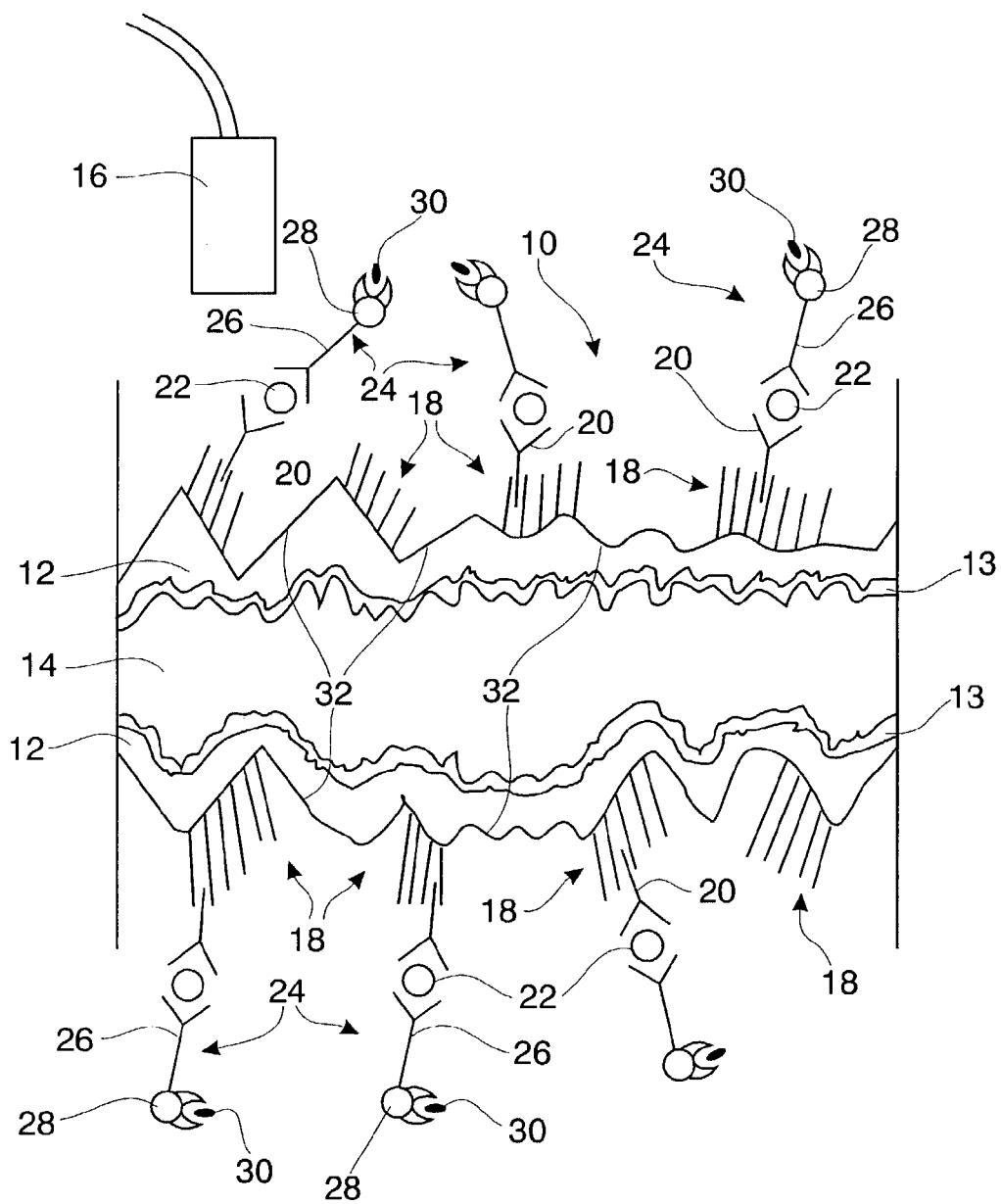
FIG. 1 shows a diagrammatic view of one embodiment of the present invention.

"Analyte" means any chemical compound, biomolecule, bacteria, virus or portions thereof susceptible to immobilization assays including immunoassays and polynucleotide hybridization assays. Analytes are generally pathogens, toxins or other microorganisms or molecules for which detection is desired. An example is the detection of the analyte *C. parvum* in drinking water.

"Sample" means a composition that may or may not include an analyte. A sample may be either aqueous, dissolved in an organic solvent or a solid sample that may be dissolved in either water or an organic solvent. Prior to being applied to microassay structures, a solid sample will need to be dissolved in a suitable solution capable of dissolving a suitable electrochemical species.

"Primary analyte binding material" refers to any of a variety of compounds and biomolecules used in immobilization assays to bind one or more analyte to a surface. These include but are not limited to primary antibodies, lipid layers, protein binding materials such as styrene, polynucleotides and combinations thereof. Primary analyte binding materials may or may not be specific for a particular analyte. For example, a primary analyte binding material may be an antibody specific for the analyte C. parvum, or may be nonspecific. For example the binding material may also be nitrocellulose, which binds all polynucleotides regardless of specific base sequences (as opposed to a polynucleotide probe that only binds to complimentary polynucleotides).

"Secondary Analyte Binding Material" is any material capable of binding to an analyte and being covalently bound to an electroactive complex. This includes secondary antibodies as used in ELISA's and polynucleotide probes as used in hybridization assays. Unlike the primary analyte binding material, it is usually preferable for the secondary analyte binding material to have specificity. Nonspecific binding is generally not desirous for the secondary analyte binding material.

"Assay Structure" refers to any structure suitable for performing the electrochemical detection and immobilization assays described below. This includes any of the assay structures disclosed ranging from centimeter scale to nanometer scale devices. An assay structure comprises at least one surface to which an analyte binds and at least one electrode for detection of current.

"Specificity" refers to the characteristic inherent to various molecules that allows them to recognize and bind to a specific molecule. For example, all antibodies are specific for a certain antigen. Also, any single stranded polynucleotide has specificity for a complimentary strand because it will not anneal to a non-complimentary strand. The specificity of antibodies, DNA probes, enzymes and substrates are what make the majority of chemical detection assays possible.

"Heat Shock Polynucleotide" refers to polynucleotides, particularly, mRNA, that are produced in higher concentrations when a microorganism is exposed to increased temperature. Those skilled in the art will appreciate that practically all living organisms increase transcription of various mRNA's upon exposure to heat. Heat shock polynucleotides are released into the solution surrounding a microorganism upon heat shock as a result of the rupturing of the cell membrane.

"Self Assembled Monolayer" and "SAM's" refer generally to a lipid monolayer that spontaneously attaches to a surface. In the preferred embodiment disclosed below, the hydrophilic component of the lipid includes a sulfide that covalently bonds to gold. A hydrophobic tale is attached to the hydrophilic region, thus forming a lipid. These lipids are capable of self assembly.

"Chip" and "Macrochip" refers generally to silicon and ceramic chips upon which an assay structure is formed that are generally on the centimeter scale. These are generally distinguished from microscale assay structures that are on the millimeter or smaller scale.

"Dip-Chip" refers to an assay structure that is suitable for being inserted directly into an aqueous solution to be tested. Utilization of a dip-chip eliminates the need for collection of a sample. The assay is performed by placing the dip-chip assay structure directly into water at a water treatment plant, lake, stream, etc., and then transferred to a container suitable for application of a secondary analyte binding material and current detection. This is distinguished from other assay structures onto which a sample of the solution to be tested is placed.

"Electroactive Complex" refers to any molecule capable of generating an electric current upon proper activation. Electroactive complexes include, but are not limited to, metalloproteins, dendrimers having multiple bound ions, redox enzymes and other molecules that are capable of either releasing a charged ion into solution or reducing a substrate. Electroactive complexes will be more further defined below.

"Activation" and "Activating" when written in reference to activating of electrochemical complexes refers generally to the act of inducing the electroactive complex into generating a current. In the case of a redox enzyme, activation is achieved by addition of the substrate to be reduced. Metalloproteins may be activated by changing the pH, changing the temperature, or denaturation. Those skilled in the art will appreciate that the methods listed above are only a few of a wide variety of methods of activating an electroactive complex.

"Electrolabeling Molecule" refers generally to a secondary analyte binding material having an electroactive complex covalently attached to it. Those skilled in the art will appreciate the terminology of electrolabeling as similar to that of radiolabeling. In the present invention, one of the novel features is electrolabeling as opposed to radiolabeling or flourescent tagging.

Those skilled in the art will recognize that there are least two current detection methods that utilize a primary and secondary analyte binding material. Perhaps the most common is the "ELISA," utilizing a primary antibody and a secondary antibody. The difference between the present invention and the current ELISA schemes is the present invention's utilization of an electrochemically active molecule. Existing ELISA's utilize a flourescent tag, an isotope label or enzymes that act upon a substrate to cause a color change. These existing methods are substantially less accurate and more time intensive than the present invention.

Another known detection method is the hybridization assay. A DNA probe is attached to an assay structure and is complementary to a polynucleotide analyte. A secondary probe is then added to the assay and binds to the analyte polynucleotide. These hybridization assays are subject to the same shortcomings as current ELISA assays. They are less accurate and more time intensive than the present invention.

Those skilled in the art will recognize that a variety of electrochemically active molecules will be suitable. The present invention contemplates the use of redox enzymes as well as metalloproteins. A redox enzyme, such as alkaline phosphatase, reduces a substrate. The reduced substrate is then oxidized by a working electrode, thereby creating a current. The substrate is again reduced by the electrochemically active enzyme and cycles back to the electrode. This redox cycling amplifies the current and allows for detection of extremely low concentrations of analyte. Those skilled in the art will appreciate that alkaline phosphatase is only one of many suitable redox enzymes. Any enzyme capable of rapidly reducing its substrate will be a suitable enzyme. In addition to redox enzymes, metalloproteins are also especially well suited for the present invention.

Those skilled in the art will recognize that there are a wide variety of both proteins and organic compounds capable of binding to metal ions. There are a number of well studied metalloproteins capable of binding to various metals such as iron, zinc, magnesium and copper to name a few. The genes that encode for these proteins may be attached to a secondary antibody in the same way that enzymes are attached to secondary activating antibodies. After the secondary antibody binds to the analyte and the assay structure is rinsed, the metalloprotein is treated so that it releases the metal ion incorporated within it. The metal ion attached to the metalloprotein may be released in a variety of ways, depending on the protein used. Some metalloproteins release the incorporated metal ion upon a change in pH. This may be accomplished either by adding buffer to the solution or utilizing the electrodes within the microcavity themselves to release protons in the solution electrolitically. Other metalloproteins release their metal ions upon reaction with a secondary compound that may be added to the immuno assay subsequent to the rinsing step. Other metalloproteins release their metal ions in the presence of chelating agents, such as ethylenediaminetetraacetic acid (EDTA). Those skilled in the art will recognize that these methods of coaxing metalloproteins to release their incorporated metal ions are well known to those skilled in the art. It will also be recognized to those skilled in the art that the addition of a metal releasing step involving pH adjustment or the addition of a compound may be incorporated into an immuno assay without any significant difficulty.

It may also be desirable to synthesize novel electroactive complexes to attach to the secondary antibody. Those skilled in the art of protein engineering will recognize that there a number of common amino acid sequences capable of binding to metal ions. A Few examples are zinc fingers, cysteine loops, heme groups and the His $X_3$ His and His Pro Phe His sequences. These amino acid sequences may be added to existing, known polypeptides or may be incorporated into novel peptide sequences and spliced onto secondary antibodies. So long as the electroactive complex is capable of forming a stable bond with a metal ion and may be induced to release the metal ion by the addition of a compound, change in pH, change in temperature or other means easily adaptable for use with assay structures.

One of the advantages of using a metal binding electroactive complexes is that it provides a metal ion that easily cycles between electrodes. This creates an automatic redox cycling reaction. Because of this, amplification is inherent to the assay. This eliminates the need for additional chemical amplification steps. Those skilled in the art will realize that this greatly simplifies chemical detection.

There are a variety of metalloproteins known to the field of biochemistry. These include metallthionin, ferritin, heme, dendrons, and staph nuclease. Those skilled in the art will recognize that these are only a very few of the many polypeptides capable of binding to metal ions. When using one of these polypeptides as an electroactive complex it may be desirable to splice or covalently bind several copies of the carrier species gene to the end of the secondary antibody gene. This would form a polypeptide polymer tail on the secondary antibody and increase the number of metal ions for use in the microimmunoassay sensor. Metalloproteins are especially well suited for redox cycling amplification by means of a counter electrode.

Those skilled in the art will appreciate that there are sundry activating agents. Which one is used will depend on the electroactive complex used. It is known that some metalloproteins release metal ions when the pH of the solution is altered. Other metalloproteins release metal ions when other parameters are changed. These parameters include, but are not limited to, change in temperature, addition of a substrate or ligands, application of an electrical current and application of electromagnetic radiation. Which metalloprotein and which activating agents are utilized will depend on a variety of factors including, but not limited to, the analyte being studied, the material utilized to immobilize the analyte, reaction temperature, reaction pH and the concentrations of various reagents and other ingredients in the solution.

The electrochemical detection assays described herein are superior to existing methods for detecting water born pathogens. This invention is especially suitable for detecting pathogens such as *Cryptospiridium parvum*. Those skilled in the art will appreciate that it is also suitable for detection of other pathogens as well as toxins such as botulinum.

The present invention maybe performed in both large and small volumes. When the present invention is incorporated into a dip-chip, it is technically being performed in an entire lake or stream. Generally, smaller volumes are preferred. The smaller the volume, the shorter the distance between the electroactive complex and the electrode. This results in shorter distance on which reduced substrates or ions must travel. In addition, smaller volumes generally provide for greater sensitivity and accuracy in quantitative detection. To this end, it is contemplated that the present invention is especially suitable for use in very small microstructures such as microcavities and micropores. Such structures are described in detail in the applications of which this is a continuation-in-part. Use of ceramic "tape" is a relatively simple and very cost effective method of forming assay structures that are suitable for the present invention. These are described in more detail in Example 3. Another bonus of using low temperature co-fired ceramics is that these devices have relatively rough surfaces when viewed on the nanoscale level. This, in turn, causes very rough surfaces on gold layers applied to them. Because the surface is rough, primary analyte binding materials attached to the surface via self assembled monolayers do not completely cover the gold surface. Small patches of unmodified gold surface remain across the gold layer. This allows the gold layer to be used as an electrode as well as an analyte binding surface. Because of the unique properties, ceramic assay structures are very desirable. The existence of gold electrode patches interspersed throughout the analyte binding surface allow for very short distances between the electroactive complex and the electrode. This allows for very accurate and rapid detection as well as a very economical method of manufacture. Those skilled in the art will appreciate that the present invention represents a significant advance in the technology of detecting *C. parvum* and other water born pathogens. Of course, those skilled in the art will also appreciate that the present invention may also be applied in non-aqueous solutions. However, the present invention is most useful in detecting water born pathogens and toxins. This provides for cleaner, safer drinking water and will reduce fatality rates worldwide.

FIG. 1 shows a schematic diagram of the present invention performed on a ceramic chip. Such ceramic chips may be placed in a container, such as a small flask, in order to form an assay structure. Alternatively, such ceramic chips may be utilized as dip-chips. Dip-chips may be placed directly in solution.

Referring to FIG. 1, assay structure 10 is comprised of ceramic chip 14. The chromium adhesion layer 13 is applied to ceramic chip 14 by thermal evaporation, sputtering or other techniques known in the art. Adhesion layer 13 aids in the application of gold layer 12. In this particular embodiment, chip 14 is comprised of ceramic. However, other materials also serve as suitable substrates for an assay structure. Silicon oxide is another suitable substrate for application of chromium adhesion layers and gold layers. Ceramic has the unusual advantage of having a rough surface that facilitates use of a gold layer as both an immobilizing surface and an electrode. In this particular embodiment, both sides of the ceramic chip have been coated. It is also possible to coat only one side of a chip. In this particular embodiment, gold layer 20 is used as the immobilizing and electrode surface. Those skilled in the art will appreciate that other metals may be used.

Other conductive metals, such as copper, are also suitable for the present invention. Any metal upon which lipid monolayers may self assemble and covalently bond and is capable of conducting electricity are suitable metals for formation of the conducting layer.

Once conducting layer 20 has been applied to the chip, lipids capable of forming self assembling monolayers are applied to the chip. These form monolayer regions 18. Because the surface is rough, only a portion of the surface is covered in lipid monolayers. This results in the chip having patches of monolayers 18 and patches of conducting surfaces 32. After the monolayer regions 18 have been formed on the assay structure 10, primary analyte binding material antibodies 20 are then attached to monolayer regions 18. In this particular embodiment, primary analyte binding material 20 is an antibody. It is also possible to use a variety of other primary analyte binding materials. Some of these will not require a monolayer in order to attach to the assay structure. The primary analyte binding material usually has specificity such that it binds only to a particular analyte. In some cases, however, it may be easier or less expensive to utilize a primary analyte binding material that binds to an entire class of biological molecules. It is possible to have binding materials that bind to any protein, any polynucleotide, any lipid, etc. In this particular embodiment, primary analyte binding material 20 is an antibody specific to analyte 22.

Once the primary analyte binding material 20 has been attached to assay structure 10, a sample that potentially has analyte in it may be applied to the assay structure. The analyte 22 will bind to primary analyte binding material 20. After sufficient time has been allowed for analyte 22 to bind to primary antibody 20, assay structure 10 may be rinsed. The rinsing step is not necessary. However, it is often preferred. One of the advantages of the present invention is that it is not necessary to rinse the assay structure after application of the sample. Other detection techniques, such as the use of flourescent tags, require rinsing in order to facilitate detection of the analyte.

Once the analyte 22 has had time to bind to antibody 20, electrolabeling molecule 24 is added to the solution surrounding the assay structure. Electrolabeling molecule 24 has at least two components, a secondary analyte binding material 26 and an electroactive complex 28. In this particular embodiment, secondary analyte binding material 26 is comprised of a secondary antibody specific to analyte 22. Secondary analyte binding material 26 must have specificity for analyte 22. Electroactive complex 28 in this particular embodiment is a metalloprotein. Metalloprotein 28 has a metal ion 30 incorporated within it. Metalloprotein 28 releases metal ion 30 upon an increase in alkalinity of the solution. Once electrolabeling complex 24 has had sufficient time to bind to all analyte 22 present in the solution, assay structure 10 is rinsed. This rinsing step is necessary in order to remove excess electrolabeling molecules that are not bound to analyte.

Because in this particular embodiment, the ceramic chips with rough surfaces is being used, an added sonication step is required. This is necessary because electrolabeling molecules may be stuck in pockets and grooves within the surface. Sonicating the chip for at least one minute is by far the most effective method of removing unbound electrolabeling molecules. When using other materials for the assay structure in which the surfaces are smooth, the sonication step is unnecessary. After sonication, the electroactive complex is activated by raising the pH to a level sufficient to cause the electroactive complex to release the metal ion. Those skilled in the art will appreciate that there is a plethora of alkaline chemicals that may be used to raise the pH. Once ions 30 are released from electroactive complex 28, they will travel to electrode surfaces 32 and release at least one electron, thereby generating a current. A potentiostat is attached to gold surfaces 12 in order to measure this current. Alternatively, electrode 16 may be utilized to measure the current generated by released ions 30. One of the advantages of using a ceramic material for the assay structure is that it provides for electrode surfaces 32. These are very close to the electrolabeling molecules, thereby reducing the time it takes for ions 30 to travel from the electroactive complexes 28 to electrode surfaces 32. The current measured is directly related to the amount of analyte present and may be used for sensitive and accurate quantitative analysis.

EXAMPLE 1

Immobilized Enzyme Linked DNA-hybridization Assay with Electrochemical Detection for *Cryptosporidium parvum* hsp70 mRNA The approach described here is a DNA hybridization assay using a novel method of electrochemically detecting viable oocystes. It introduces several new features and solves many of the problems that were previously reported. The assay detects hsp70 mRNA of *C. parvum* (and the DNA gene for mRNA), thereby providing a way to detect viable organisms. The transcription of hsp70 mRNA is induced by subjecting the oocyst to heat shock. This substantially amplifies the hsp70 mRNA concentration and allows the detection of low concentrations of the oocyst. The method of immobilizing the primary probe involves covalent attachment (through amide formation with self-assembled monolayers, SAMs, of 11-mercapto-1-undecanol on gold) and provides for a detecting electrode separate from the hybridization surface (no electron transfer events through the modifyied layer). This improves stability of the modified surface. Because the detecting electrode is bare (not modified), a maximum signal is observed. The assay is based on known hybridization methods that utilize complementary sequences of a primary probe ($P_1$), the target polynucleotide (T), and a secondary probe ($P_2$), but uses alkaline phosphatase (AP) conjugated to $P_2$ to produce an electrochemically active species (p-aminophenol, $PAP_R$, from p-aminophenyl phosphate, PAPP) for detection at the electrode that amplifies with time, as opposed to intercalation of electroactive molecules, direct detection of guanine residues, fluorescent labels or radioactive tags. The assay may be miniaturized and incorporated with LTCC chips or microstructures. This drastically improves assay time and detection limits, as demonstrated for electrochemical detection of IgG using microcavity devices in Example 1.

The primary probe, $P_1$ is a 33-mer oligonucleotide SEQ ID NO: 1 5'-3' TAT AGG GAG AAG GTA GAA CCA CCA ACC AAT ACA containing a 20-base sequence that is complimentary to the target DNA (T) and a C6 amino linker at the 5' end that serves as a spacer from the macrochip. The secondary probe consists of SEQ ID NO: 2 ACA TCA TGT ACA GAT CTC TTG TCC CGC AAC TAC GAA GGT CTG, 42-mer oligonucleotide labeled with alkaline phosphatase, $P_2$~AP at the 5' end. It has 24 bases complimentary to the 3' end of the target DNA. The target DNA (5'-3' sequence 1039 to 1082 of U71181: SEQ ID NO: 3 GGA CAA GAG ATC TGT ACA TGA TGT TGT ATT GGT TGG TGG TTC TA)[1] is a 44-base oligomer that is specific for *C. parvum* hsp 70 mRNA. Target sequence 1063 to 1082 is complimentary to $P_1$ while 1039 to 1062 is complimentary to $P_2$-AP. Oligonucleotides for the hsp70 of *E. coli*, heat shock protein 60 of *Campylobacter lari*, heat shock protein gene of *Giardia lamblia*, heat shock protein gene of *Listeria monocytogenes*, and DNA of *Salmonella typhi* were tested for cross reactivity. The oligonucleotide sequences are chosen with the maximum region of homology to the hsp70 mRNA gene of *C. parvum*. The *C. parvum* oocysts at a concentration of $0.26 \times 10^6 \pm 0.05$ oocysts per mL (heat shocked for 10 min at 43° C. by the supplier and heat shocked for additional 10 min at 43-45° C. in our lab), *Cryptosporidium muris* oocysts at a concentration of $0.26 \times 10^6 \pm 0.05$ per mL (heat shocked for 10 min at 43° C. by the supplier and heat shocked for additional 10 min at 43-45° C. in our lab), and *Giardia lamblia* cysts at a concentration of $0.26 \times 10^6 \pm 0.05$ per mL (heat shocked for 10 min at 43° C. by the supplier and heat shocked for additional 10 min at 43-45° C. in our lab) were obtained from Waterborne, Inc. (New Orleans, La.). *E. coli* and *S. aureus* were streaked in nutrient agar plates and incubated at 37° C. for 24 h. mRNA from heat shocked *E. coli* was isolated and detected using Tri Reagent and FORMazol (Molecular Research Center, Inc., Cincinnati, Ohio).

A gold coin (Canadian Maple Leaf, 99.99%) and a chromium-plated tungsten rod (R. D. Mathis, Long Beach, Calif.) served as sources for metal deposition. Silicon wafers (125 mm diameter and 365-406 mm thick) with crystal orientation of (100) were obtained from Wacker Siltronic Corp. (Portland, Oreg.). Polyimide (PI-2721, HD MicroSystems, Du Pont) was used according to DuPont specifications.

The buffer solutions are as follows: (a) PBS=0.1 M $KH_2PO_4$ and 6.2 mM $Na_2HPO_4$ in 14.3 mM NaCl at pH 6.0; (b) 20×SSC/BSA=1 mg/mL BSA, 0.5 mg/mL 2-chloroacetamide, 173.5 g/L NaCl, 88.2 g/L sodium citrate, 200 mg/L SDS, and 200 mg/L sodium azide, pH 7.6 (adjusted with 6 M HCl or 6 M NaOH); (c) 10 mM TE buffer=10 mM Tris-HCl, 1 mM EDTA, pH 8.0; (d) 0.1 M Tris=0.10 M Tris, 1 mM magnesium chloride, and 0.02% (w/v) sodium azide, pH 9.0 (adjusted with 6 M HCl or 6 M NaOH).

Au macrochips (~1.4 cm×~1.2 cm for electrodes, where the electroactive area is about 0.6 to 1 $cm^2$, and 1.2 cm×1.2 cm for surface modification) were made from a 125 mm diameter silicon wafer substrate that had 1.4 to 1.8 mm $SiO_2$ deposited on both sides at 250° C. by plasma enhanced chemical vapor deposition (PECVD, Plasma Therm System VII). Deposition of a 15 Å adhesion layer of Cr and 1000 Å of Au was carried out using an Edwards Auto 306 TURBO thermal evaporator (Edwards High Vacuum Instrument International, West Sussex, UK) to fabricate Au macrochips. Polyimide macrochips (1.2 cm×1.2 cm) were made using the Au-coated silicon wafer as the starting substrate. They were spin-rinsed-dried (SRD) using ST 270D (Semitool, Calif.) for a total of 400 s before spin-coating the polyimide to form a 4-mm thick layer. Cross-linking involved exposure to UV light at 350 nm for 12 s and curing at 150° C. for 30 min and at 250° C. for an additional 30 min. This process completely covers the Au macrochip with polyimide so that the metal does not influence subsequent surface-modification experiments. The Au-coated and polyimide-coated silicon wafers were diced to size by hand using a diamond scribe.

The Au macrochips were cleaned in piranha solution (30:70 (v/v) of 30% $H_2O_2$ and concentrated $H_2SO_4$) for 30 min and thoroughly rinsed for 30 min with running DI water before use.

SAM preparation, rinsing, and drying were carried out completely in an Ar-purged glovebag after the cleaning step to eliminate oxidation of SAMs by air or ozone. The cleaned Au macrochips were soaked in solutions of 4 mM MUA in Ar-purged ethanol for 24 h to form SAMs, followed by rinsing with Ar-purged ethanol three times in each of three separate test tubes inside the glovebag. The chips were dried with Ar and kept in Ar-filled closed vials before use.

A working solution of 50 mg/mL $P_1$ (unless otherwise indicated) and 0.1 M EDC in PB was prepared by combining appropriate volumes of stock solutions of 1000 mg/mL $P_1$ in 10 mM TE buffer and 0.2 M EDC in PB, followed by dilution with PB buffer. All of the following steps for $P_1$ immobilization were performed inside a glove bag filled with Ar. MUOL SAM-modified macrochips were soaked in 500 mL of the $P_1$/EDC working solution inside a capped polypropylene centrifuge for 2 h. The EDC assists covalent attachment of $P_1$ to the free end of the SAMs. The chips were rinsed three times with 2×SSC and then soaked three times in 1×SSC for about 15 min each.

Working solutions of 50 mg/mL T (unless otherwise indicated) were prepared by dilution of a 1000 mg/ml T in 10 mM TE buffer with 20×SSC/BSA. The $P_1$-immobilized macrochips were exposed to a 500 mL solution of 50 mg/mL T inside a Parafilm sealed Petroi plate to prevent evaporation for 1 h. The $P_1$+T immobilized macrochips were soaked and shaken three times with 1 mL of 2×SSC for 30 min followed by 1 mL of 1×SSC for 15 min.

A working solution of 50 mg/mL $P_2$-AP (unless otherwise indicated) was prepared by diluting a 1000 mg/mL $P_2$-AP stock solution in 10 mM TE buffer with 20×SSC. $P_1$-immobilized macrochips that had been exposed to T and rinsed, were subsequently exposed to 500 mL of the $P_2$-AP working solution for 3 h and then rinsed by soaking three times in 5 mL of acetate TBSA for 15 min each to eliminate non-specifically adsorbed $P_2$-AP. These steps were performed outside of the glovebag inside Parafilm sealed Petri plates to prevent evaporation.

The enzyme substrate solution was 4 mM PAPP in 0.1 M Tris at pH 9.0, as previously described. The PAPP solution was purged with Ar and kept from light to minimize oxidation. Macrochips, containing the complete hybridization assembly, were rinsed three times with 5 mL of 0.1 M Tris at pH 9.0 at 10 min each before soaking in 5 mL of Ar-purged (15-30 minutes) PAPP solution in a sealed beaker wrapped in aluminum foil inside a glove bag filled with Ar for 12 h.

A BAS-100 B potentiostat fitted with a PA-1 preamplifier (Bioanalytical Systems, Lafayette, Ind.) or a CH Instruments Electrochemical Workstation Model 650A potentiostat with a Picoamp booster and Faraday cage (CH Instruments, Inc, Austin, Tex.), controlled by a PC with CHI-650A software were used to perform cyclic voltammetry (CV). The electrochemical setup involved Au macrochip working, Pt flag counter, and Ag/AgCl (saturated KCl) reference electrodes in a 25-mL screw cap beaker. Initial electrochemical characterization of working electrodes was performed in a solution containing 4 mM $K_3Fe(CN)_6$ in 0.1 M KCl and 4 mM PAP or PAPP in 0.1 M Tris, pH 9.0.

Activity of the enzyme linked DNA-hybridization assay at macrochips of Au, (and at macrochips of bare and double-sided polyimide-coated silicon wafer for nonspecific adsorption studies) was determined by evaluating the surrounding PAPP solution for $PAP_R$. Working electrode potentials were kept within appropriate ranges to avoid electrochemical conversion of PAPP into $PAP_R$. The Au underlying the modifying layer containing assay components was never used to detect the enzymatically-generated $PAP_R$.

*C. parvum* oocysts, *C. muris* oocysts, and *Giardia lamblia* cysts that were initially heat shocked by the vendor (microscopic analysis by vendor after heat shock showed 7% excystation or rupture of the oocysts) in water bath for 10 min at 43° C., were diluted to $2 \times 10^3$ oocyst/mL from the $0.26 \times 10^6 \pm 0.05$ oocysts per mL stock solution with 10 mM TE buffer in a 1.5 mL centrifuge tube. The $2 \times 10^3$ oocyst/mL diluted oocysts was further heat shocked to release mRNA inside the cells by placing the tube in a beaker of water at 43-45° C. for 10 minutes. Products of the heat shocking, presumably the mRNA, were analyzed using the same procedures as those for the C. parvum target DNA, using $P_1$ and $P_2$-AP at 50 mg/mL.

E. coli and S. aureus, both heat shocked and not heat shocked were evaluated. E. coli and S. aureus were prepared in the laboratory by streaking on agar plate and incubating at 37° C. for 24 hours. A single colony of either organism was scraped and dissolved in 1 mL of 10 mM TE buffer in a 1.5 mL centrifuge tube and used as the target for the DNA-hybridization assay. A duplicate of the solution of each organism was heat shocked in a beaker of water at 43-45° C. for 20 minutes. The resulting heat shocked solution was used as the target following the procedure for the DNA-hybridization assay for C. parvum⁻, using $P_1$ and $P_2$-AP at 50 mg/mL.

A colony of E. coli dissolved in 1 mL of TE buffer was heat shocked in a beaker of water at 43-45° C. for 20 minutes and treated with 1 mL Tri Reagent to isolate the RNA. A 400 mL drop of chloroform was subsequently added. The solution was vortexed for 15 seconds and allowed to stand at room temperature for 15 minutes before centrifugation at 10,000 g for 10 minutes. The aqueous phase was pipetted out into a new tube and treated with 0.5 mL isopropanol. The solution was stored at room temperature for 5 minutes and then centrifuged at 10,000 g for 8 minutes. The RNA was a gel-like pellet that settled at the bottom of the tube. 1 mL of 75% ethanol was added to the RNA pellet and subsequent centrifugation at 7,500 g for 8 minutes. The ethanol was removed and the pellet was air dried at room temperature. The RNA was dissolved in 1 mL FORMazol and incubated for 10 minutes at 55-60° C. before the absorbance at 260 and 280 nm was measured using a diode array spectrophotometer. RNA preparation gives $A_{260/280}$ between 1.6 and 1.8.

To evaluate the effect of $P_1$ coverage, the assay was carried out using chips modified with $P_1$ from solutions having concentrations of 5 mg/mL to 75 mg/mL. Fixed concentrations of T and $P_2$-AP at 50 mg/mL were used in these studies.

Figure 2:
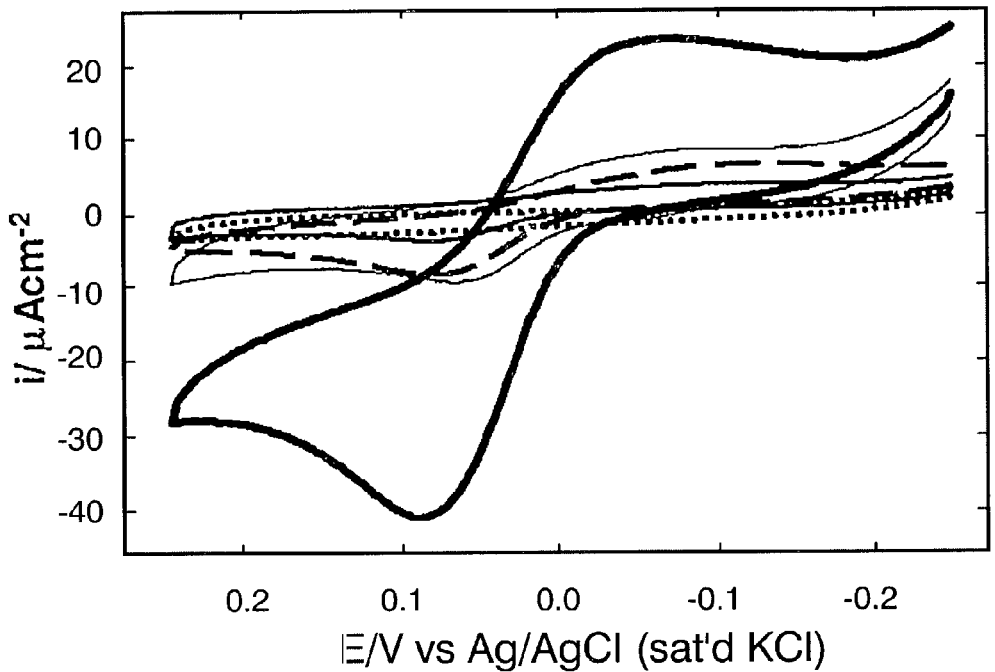
FIG. 2. Comparative activities of modified surfaces on macrochips coated with gold on one side. CV responses (50 mV/s) to enzymatically-generated $PAP_R$ were obtained in 4 mM PAPP in 0.1 M Tris buffer after 12 h incubation of MUA-SAM-modified macrochips. The complete assembly (EDC-coupled $P_1+T+P_2$~AP, thick solid curve) resulted in the largest signal. Other signals are for incomplete assemblies: no T (EDC-coupled $P_1+P_2$~AP, medium solid curve), no $P_1$ (T+$P_2$~AP, thin solid curve), neither $P_1$ nor T ($P_2$~AP, dashed curve), and PAPP without modified chip (dotted curve).

To evaluate the effect of $P_2$-AP, assays at concentrations of 5 mg/mL to 75 mg/mL (based on the mass of the unconjugated $P_2$) were prepared with fixed concentrations of T and $P_1$ at 25 mg/mL. MUOL SAMs as a platform for DNA immobilization are known in the art. However, this is the first report of using MUA SAMs for immobilizing a DNA probe to gold surfaces in an enzyme linked DNA hybridization assay for detecting C. parvum hsp70 mRNA. The activity of modified surfaces was investigated by soaking macrochips coated with gold on one side in a solution of 4 mM PAPP in 0.1 M Tris for 12 h and detecting the enzymatically-generated $PAP_R$ amperometrically at a nearby bare gold working electrode with a Pt auxiliary and Ag/AgCl (saturated KCl) reference electrodes. FIG. 2 shows the results. The largest current was obtained when the complete assembly was involved. Small currents (10-25% of that for the complete assembly) were obtained for incomplete assemblies. This small signal appears to be due to nonspecific adsorption on the silicon dioxide-coated side of the macrochips.

Studies were performed to identify the extent of non-specific adsorption on silicon dioxide, polyimide, and gold. Minimizing nonspecific adsorption is important to avoid false positives and high background results in an assay. Tests were performed to determine which surface is prone to non-specific adsorption of the assay complete and incomplete assembly. The PAP signal from double-sided gold macrochip is almost twice that from a silicon wafer coated only on one side with gold. This is due to a small degree of non-specific adsorption on the silicon wafer as shown by the signal from the bare silicon wafer. The polyimide macrochip gave no significant signal showing the absence of nonspecific adsorption.

Environmental and drinking samples of water taken from the source may contain mRNA from naturally occurring microorganisms that can interfere with the DNA-hybridization assays for hsp70mRNA of C. parvum. Cross reactivity of the assay was performed on heat shocked and not heat shocked naturally occurring microorganisms to determine selectivity of the assay. Synthetic DNA for hsp mRNA or the gene of naturally occurring pollution indicator and pathogenic organisms and samples of heat-shocked cells of whole organisms were assayed to determine interferences. The synthetic DNA, which is a purified target that is easily obtainable from commercial vendors, binds to $P_1$ and $P_2$ equally well as the mRNA for which it codes because of its composition. The purified target allows assessment of the assay for the oligonucleotide without complications from other cellular components. The section of synthetic DNA from other organisms was chosen based on the largest number of overlapping sequences with $P_1$ and $P_2$. Samples of beat-shocked whole organisms allow evaluation of the extent of interferences from cellular components. The organisms were heat shocked twice to ensure rupture of cellular membranes that leads to emergence of the mRNA analyte into the surrounding fluid to make it accessible for detection.

Figure 3:
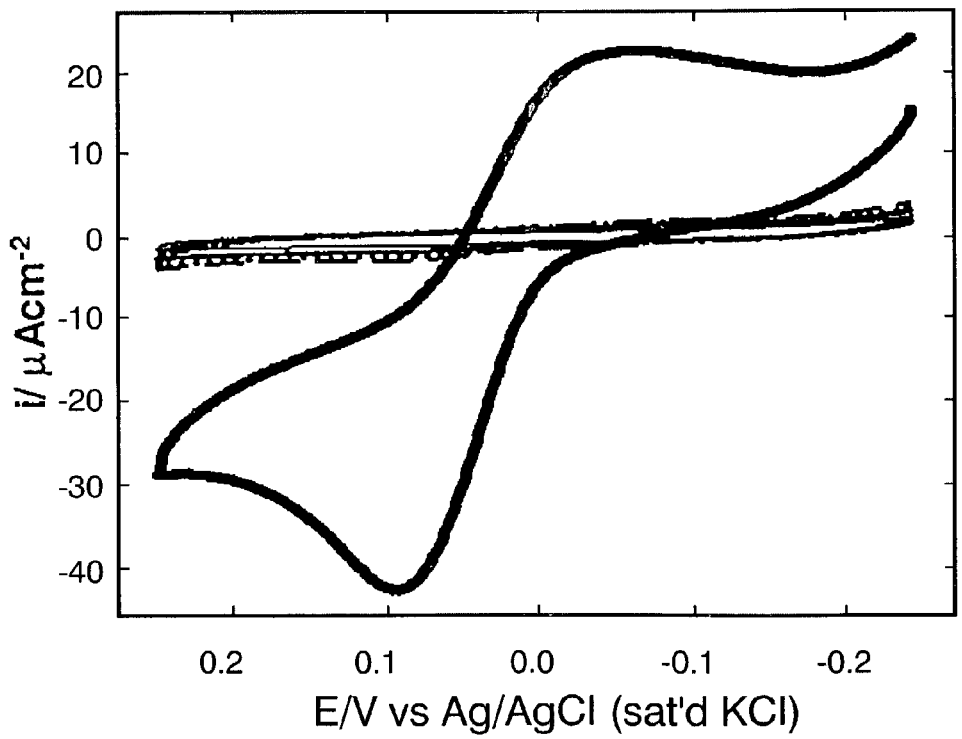
FIG. 3. Cross reactivity tests of assay using double-sided gold macrochips and oligonucleotides as the target from hsp 70 mRNA gene of various organisms. CV was performed in a solution of 4 mM PAPP in 0.1 M Tris at 50 mV/s that was incubated with the modified macrochip for 12 h. The responses correspond to the following target organisms: *C. parvum* (thick solid curve), and almost complete overlap for *Campylobacter lari* (dashed curve), *Escherichia coli* (dotted curve), *Giardia Iamblia* (medium solid curve), *Salmonella typhi* (short dashed curve), and *Listeria monocytogenes* (thin solid curve). Concentrations that were used are: $P_1$=50 µg/mL, T=50 µg/mL, $P_2$-AP =50 µg/mL.
Figure 4:
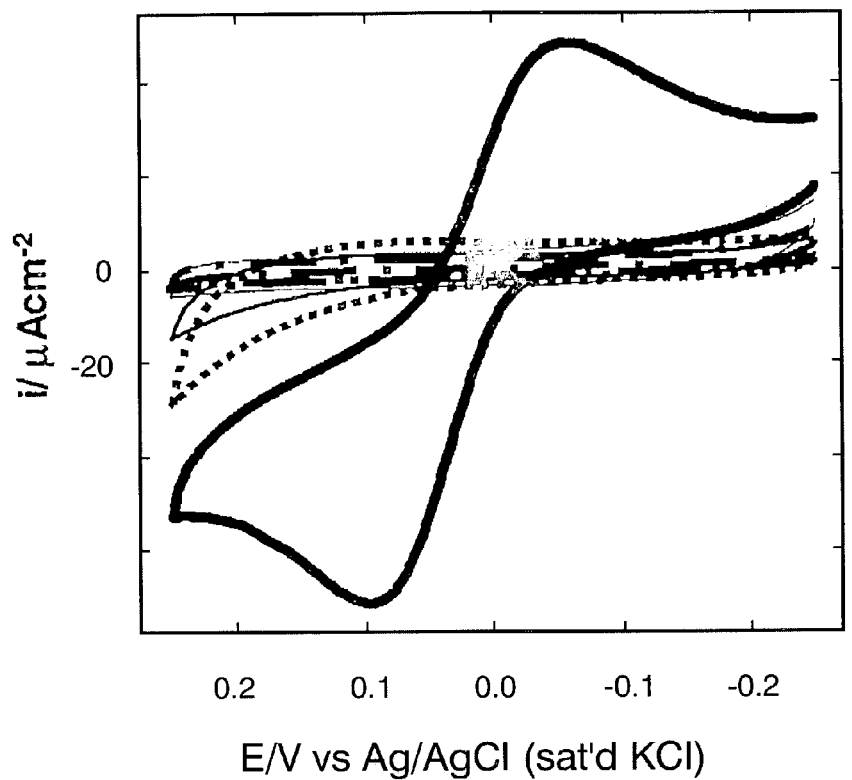
FIG. 4. Cross reactivity tests of assay using solutions of heat shocked organisms that were heat shocked a second time (unless otherwise noted) for 10 min at 43-45° C. CV was performed in a solution of 4 mM PAPP in 0.1 M Tris at 50 mV/s that was incubated with the modified macrochip for 12 h. The responses correspond to the following target organisms: *C. parvum* at $2 \times 10^3$ oocyst/ml (thin solid curve), *E. coli* heat shocked and not heat shocked at single 24 h colony/mL (complete overlap—dashed curve), and *S. aureus* heat shocked and not heat shocked at single 24 h colony/mL (complete overlap—short dashed curve).

FIGS. 3 and 4 compare results for the synthetic hsp70mRNA from C. parvum with oligonucleotide sequences from E. coli, Campylobacter lari, Giardia lamblia, Listeria monocytogenes, and Salmonella typhi. There is no significant signal for enzymatically generated $PAP_R$ from any of the other targets. Therefore, the DNA-hybridization for hsp70 mRNA is highly specific to the hsp70 mRNA oligonucleotide sequence for C. parvum.

Reactivity to heat shocked whole organisms (at conditions that were found to show a positive signal for the presence of RNA from heat shocked E. coli), other than C. parvum is also negligible under our conditions. The assay therefore is ideal for assays of real water samples where such interferents may be present.

The electrochemical signal increases linearly with $P_1$ concentration but plateaus when the concentrations of $P_1$ and T are similar. This one-to-one correspondence between $P_1$ and T suggests a quantitative immobilization of $P_1$ and T from solution. As the $P_1$ concentration in solution increases, the surface coverage on the modified macrochip also increases, as long as the maximum coverage is not reached. When the number of $P_1$ molecules on the surface exceeds the number of T molecules in the subsequent solution, all available T molecules immobilize, achieving a complete surface coverage. Thus, they hybridize to a constant number of $P_2$-AP molecules, resulting in a plateau in the electrochemical current.

The electrochemical signal increases linearly with $P_2$-AP concentration but plateaus when the concentration reaches that of the T solution. The oligonucleotides in the solutions over the macrochip are quantitatively immobilized onto the surface in a one-to-one ratio and in a form that is active. An important conclusion is that under these conditions, the assay should involve concentrations for $P_1$ and $P_2$-AP that are higher than that of T, so that the signal is proportional to the T concentration and not limited by the probe concentrations in solution.

Such complete hybridization from solution is much more rapidly achieved (within seconds or minutes) from smaller solution volumes using miniaturized devices (microliters to picoliters), such as the microstructures described herein. For example a 2-3 nL drop of solution on one of the microcavities was quantitatively electrolyzed in less than 5 min. Transfer to small devices like this greatly improves the incubation times and response times for detection.

Figure 5:
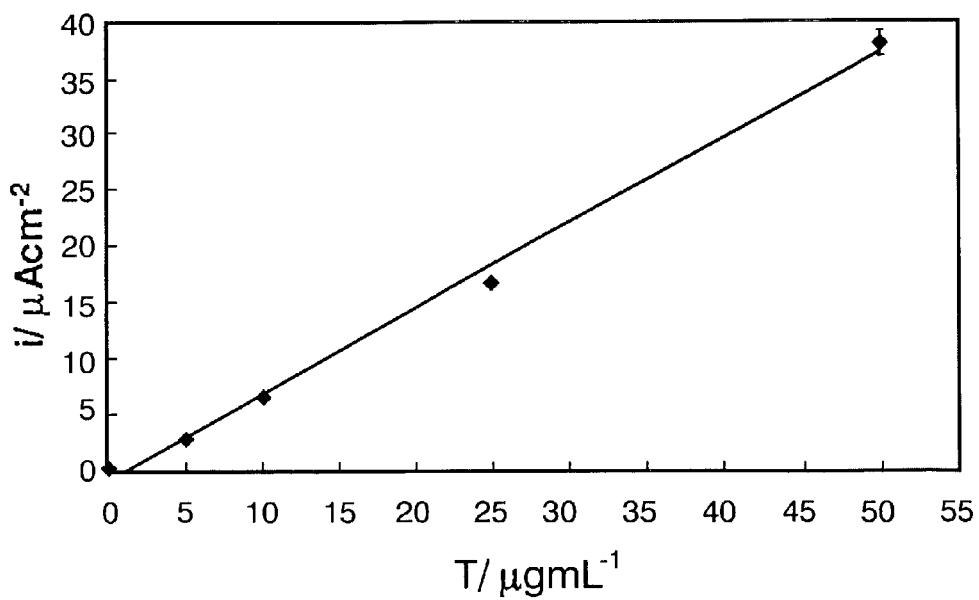
FIG. 5. Calibration curve for T at concentrations from 5 to 50 µg/mL. Peak current from CV responses at 50 mV/s for two samples at each concentration were measured. Double-sided gold macrochips were modified with the complete assembly (MUA SAMs+$P_1$+T+$P_2$-AP).

To evaluate the sensitivity and detection limit of the assay, a calibration curve over concentrations of T from 5 to 50 μg/mL was obtained (FIG. 5). Fixed concentrations of $P_1$ and $P_2$-AP were selected (50 mg/mL) so that they would not limit the signal. The peak current from CV responses (average of two measurements) is linear, giving a least squares fit of $y=0.77$ μA mL cm$^{-2}$ mg$^{-1}$×−0.97 mAcm$^{-2}$cm$^{-2}$ mg$^{-1}$, $R^2=0.99$. A limit of detection of 2 mg/mL was calculated at the 99% confidence level (t is ~3 and there are >8 degrees of freedom), where the slope from the calibration curve is 0.77 mg/mL±0.02 mAmLcm$^{-2}$mg$^{-1}$,mL and the standard deviation from the blank signal (10 measurements) from 5 mL of 4 mM PAPP is 0.56 mAcm$^{-2}$. This limit of detection is lower than previously reported by others. Furthermore, our technique is better because our detecting electrode is independent of the modified surface giving a better and higher signal, our system can distinguish viable oocysts from non-viable oocysts, and we have a lower detection limit.

Based on the forward peak current of 4000 mA/cm$^2$ generated from 4 mM PAP, only ~1% of the 4 mM PAPP is enzymatically converted by the complete assembly on the modified surface. This shows that both higher and lower concentrations of the hsp70 mRNA oligonucleotide can be detected using this system. Using the present invention, a bioassay for mouse IgG takes less than 30 min to both complete the assembly of immunoassay components onto the antibody-modified surface and detect enzymatically-generated species. Enzymatic conversion of the substrate p-aminophenylphosphate to p-aminophenol is detectable in less than 30 s using cyclic voltammetry at a gold, tubular nanoband electrode immediately adjacent to the modified RMD. With the DNA detection scheme for *C. parvum* described here, the assay time decreases down to less than an hour including the constraint in the amount of the time required for DNA-hybridization. The limit of detection for the 13 kilodalton hsp70 mRNA for *C. parvum* in the microcavity is order of magnitude lower.

EXAMPLE 2

Immobilized Enzyme Linked Immunoassay with Electrochemical Detection for *Cryptosporidium parvum* Oocysts A typical sandwich-type immunoassay was performed in which a monoclonal IgM antibody to *C. parvum* was covalently attached via carboduimide coupling to 11-mercapto-1-undecanol and 11-mercapto-1-undecanoic acid self-assembled monolayers on gold macrochips, followed by capture of *C. parvum* oocysts from the sample solution, and attachment of a secondary antibody, labeled with alkaline phosphatase (AP). Bare gold macroelectrode and a microelectrode were used to detect p-aminophenol enzymatically generated by the AP immobilized on the modified chip from a solution of 4 mM p-aminophenylphosphate in 0.1 M Tris buffer (pH=9). This is the first report of electrochemical detection of *C. parvum* oocysts using an immunoassay and of conjugating alkaline phosphatase to the IgM antibody of *C. parvum$_2$* oocyst. Complete assays provide a current of 45 mAcm$^{-2}$ at the macroelectrode for 10 oocysts/mL and approximately 5 mAcm$^{-2}$ for 1 oocyst/mL that is significant above background. The detection limit for the microelectrode detection was 7 oocysts/L. Incomplete modifications (where at least one component is omitted) produce a signal that is the same as background.

The advantages of electrochemical detection include the ease with which one can miniaturize devices, construct portable instrumentation, use in samples that are turbid, and yet maintain very high sensitivity. It provides a significantly better detection method for *C. parvum* oocysts in the environment, in animals and in humans. It is also readily applied to other waterborne pathogens, such as cholera, *E. coli*, and anthrax.

The previous example disclosed a DNA-hybridization approach for detecting mRNA for hsp70 of *C. parvum* oocysts with electrochemical detection. Although that method provides for detection of viable oocysts, there is still a great interest in developing alternate detection methods for whole oocysts. Selective capture of oocysts by immobilized capturing antibodies isolates and concentrates them, avoids the heat shock step, and detects both the dead and the live oocysts. Furthermore, an immunoassay can be performed in untreated water samples while a DNA-hybridization assay requires elimination of enzymes that can potentially degrade the DNA probes. Immunoassay capture and isolation of the whole oocysts prior to DNA-hybridization assay can serve the purpose of eliminating the DNA-degradation enzymes such as DNAses and RNases.

The immunoassay described herein involves immobilizing a monoclonal IgM antibody to *C. parvum* oocyst (Ab) through covalent attachment to self-assembled monolayers (SAMs) of 11-mercapto-1-undecanol (MUOL) or 11-mercapto-1-undecanoic acid (MUA) on the surfaces of gold-coated macrochips using 1-ethyl-3-[3-(dimethylaminopropyl)]-carbodiimide hydrochloride (EDC). SAMs of MUA or MUOL have been used previously for immobilization of protein and DNA. However, they have not yet been used to immobilize the monoclonal IgM antibody to *C. parvum* (Ab). The Ab captures the oocysts (the antigen, Ag) from a sample solution. Attachment of a second monoclonal IgM antibody *C. parvum* that is labeled with alkaline phosphatase (AP) completes the immobilization.

Monoclonal IgM antibodies to *C. parvum* oocyst were conjugated to alkaline phosphatase following known bioconjugation techniques. Briefly, 4 mg of AP (alkaline phosphatase) was dissolved in 400 mL of 0.1 M PBS, pH 7.4 containing 0.5 M EDC to make 10 mg/mL AP to which 100 mL of Ab stock solution at 4.7 mg/mL was added. After vortex mixing, the solution was allowed to react for 2 h at room temperature. (If precipitation occurred, the amount of EDC was scaled back until a soluble conjugate was obtained). The 1 mL conjugate was purified by dialysis against a 500 mL solution of 0.01 M sodium phosphate in 0.15 M NaCl, pH 7.4, overnight with three changes. (If some turbidity formed during the process, it was removed by centrifugation). Spectra gel absorbent was used to concentrate the dialysate down to 1 ml as follows: The dialysis tubing containing the dialysate is laid on top of 10 g of the spectra gel absorbent placed on an aluminum foil. Using a spatula, the dialysis tubing was covered with the spectra gel adsorbent. The aluminum foil is folded over the dialysis tubing to formn a pouch. After 15 minutes, the pouch is opened, the powder is wiped out from the outside of the dialysis tubing, and the dialysate is recovered and its volume is measured with a pipet.

SAM-modified macrochips were soaked in 500 mL of a solution of 48 mg/mL Ab dissolved in PBS containing 0.1 M EDC for at least 2 h inside an Ar filled glove bag. (Note that all steps in the immunoassay were performed in a glass scintillation vial to avoid physisorption of the proteins to plastic centrifuge tubes or polystyrene Petri plates. These vials were sealed tightly at all stages of the modification process to minimize evaporation). The rinsing procedure involved soaking and shaking the chips for 5 minutes in each of the following solutions: 5 mL of 1 M NaCl two times followed by 5 mL of 0.02 M PBS, pH 7.4 three times and 1 mL of DI water, to eliminate non-specifically adsorbed Ab. The macrochips were soaked in 5 mL PBS-BSA-GS for at least 30 minutes before the next step or kept overnight inside the refrigerator when not immediately used.

Ab-immobilized macrochips were exposed for 6 h to a 1 mL solution containing C. parvum oocysts (previously heat shocked at 43° C. for a total of 20 min) diluted to the desired concentration with 0.02 PBS-BSA-GS, pH 7.4 from a stock of $0.26 \times 10^{6\pm0.05}$ oocyts/mL. The rinsing process involved soaking and shaking the chips in 5 mL of PBS-BSA-GS 3 times for 5 min each, followed by 5 mL of acetate TBSA two times, and once with 5 mL DI water for 5 min, each in a glass test tube.

Macrochips that had been modified with SAMs+EDC-coupled Ab+oocysts were subsequently exposed to a 500 mL solution of Ab-AP (10 mL of synthesized Ab-AP in 1 mL 0.02 PBS-BSA-GS) for 4 h. These were rinsed 3 times with 5 mL of PBS-BSA-GS and two times with 5 mL of acetate TBSA and once with 5 mL DI water for 5 min each.

The enzyme substrate solution of 4 mM PAPP in 0.1 M Tris at pH 9.0 was purged with Ar for (15-30 min). Macrochips, containing the complete immunoassay assembly, were rinsed three times with 5 mL of 0.1 M Tris at pH 9.0 at 5 min each before soaking in 5 mL of enzyme substrate solution inside a sealed glass beaker wrapped in aluminum foil for 12 h inside a glove bag filled with Ar to minimize air and light oxidation.

A BAS-100B potentiostat and a PA-1 preamplifier with BAS-100W electrochemical software (Bioanalytical Systems, Lafayette, Ind.) and a CH Instruments Electrochemical Workstation Model 650A potentiostat with a Picoamp booster and Faraday cage (CH Instruments, Inc, Austin, Tex.), controlled by a PC with CHI-650A software were used to perform cyclic voltammetry (CV). Two types of electrochemical setups were used to perform electrochemistry of PAPP solutions after soaking the modified macrochips in them. The macro external setup contained a Au macrochip working, Pt-flag counter, and Ag/AgCl (saturated KCl) reference electrodes. The micro internal setup uses a tubular nanoband as the working electrode and the top layer Au surface served as the combined pseudoreference/auxiliary electrode. Initial electrochemical characterization of all electrodes in the microcavity was performed in a solution containing 4 mM $K_3Fe(CN)_6$ in 0.1 M KCl and 4 mM $PAPP_R$ in 0.1 M Tris, pH 9.0. Working electrode potentials were kept within appropriate ranges (from −0.15 to +0.25 V) to avoid electrochemical conversion of PAPP into $PAP_R$.

After capture, oocysts may rupture from drying while mounting or while scanning inside the SEM. It is recommended that the samples be kept in the PBS buffer to prevent drying out of the oocysts.

Figure 6:
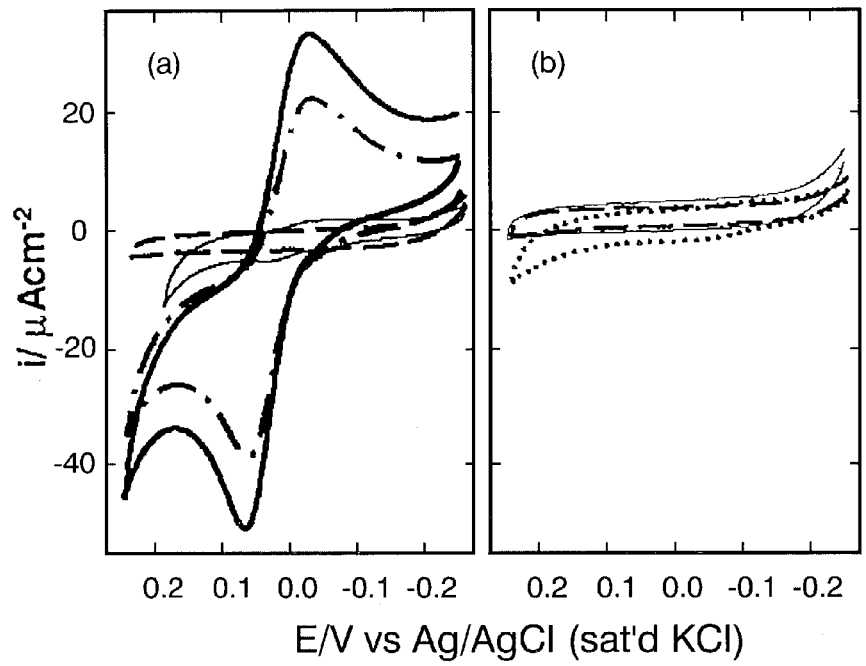
FIG. 6. Comparison of activity of macrochips that were modified with complete and incomplete assemblies of assay components. CV responses (50 mV/s) at a macro Au external electrochemical setup to enzymatically-generated $PAP_R$ were obtained in 4 mM PAPP in 0.1 M Tris buffer after 12 h incubation of the modified macrochips. Responses for the complete assemblies (SAM+EDC-coupled primary Ab+Ag+Ab-AP) are shown in (a). Those involving MUOL-SAM macrochips are: (a) 0 oocysts/mL (dashed curve), 1 oocyst/mL (thin solid curve), and 10 oocysts/mL (thick solid curve). A response from a MUA-SAM macrochip for comparison is also shown for 10 oocysts/mL (dashed-dot curve). The incomplete assemblies are shown in (b), all of which involve MUOL SAMs: no primary Ab (SAM+Ag+Ab-AP, dotted curve), neither Ag nor Ab-AP (SAM+EDC-coupled primary Ab, dashed curve), and neither primary Ab nor Ag (SAM+Ab-AP, thin solid curve).

Immunoactivity of modified surfaces was investigated by detecting the enzymatically-generated $PAP_R$ from a PAPP solution at a nearby bare electrode in an external set-up. The curves in FIG. 6 show typical CV responses. The immunoactivity of the complete assembly on MUOL SAMs, which involved 10 oocyst/mL sample gave a forward peak current of 45 mA/cm². That for 1 oocyst/mL was approximately 1/10 of that of the higher concentration, as expected, but barely above background. The latter concentration is 10 times greater than the measurable levels of the EPA approved methods. CV responses from the incomplete assemblies on MUOL SAMs are also shown in FIG. 6, but overlap with the background CV (bare gold macrochip soaked in PAPP solution). Thus, non-specific adsorption, which may yield false positives, is not a problem under these conditions. The complete assembly using MUA SAMs showed a smaller signal than the complete assembly using MUOL SAMs.

Based on the forward peak current of 4000 mA/cm² generated from 4 mM PAP, only 1% of the 4 mM PAPP was enzymatically converted by the complete assembly on the modified surface. This shows that 10 oocysts per mL down to 1 oocyst per mL concentrations can be detected using the macroelectrode system.

In order to improve the signal-to-background ratio, the macroelectrode was replaced with a microelectrode. In particular, an internal setup at a microcavity device was used, where the TNB served as the working electrode. Faradaic current at such small electrodes exceeds that of charging current due to the influence of radial diffusion and the small electrode area, respectively. A characterization experiment yielded a 63 nA plateau current at the TNB electrode in a 5 mL solution of 4 mM $PAP_R$ in 0.1 M Tris, pH 9.0. This is the maximum signal expected if the entire 4 mM PAPP solution were enzymatically converted. The plateau current for the largest concentration in this group (~1.2 nA) is only 2% of that for a completely converted solution, yet is well above background. The signal-to-noise ratio is also far better than that obtained for 10 times the oocyst concentration using the macrochip detection setup.

Figure 7:
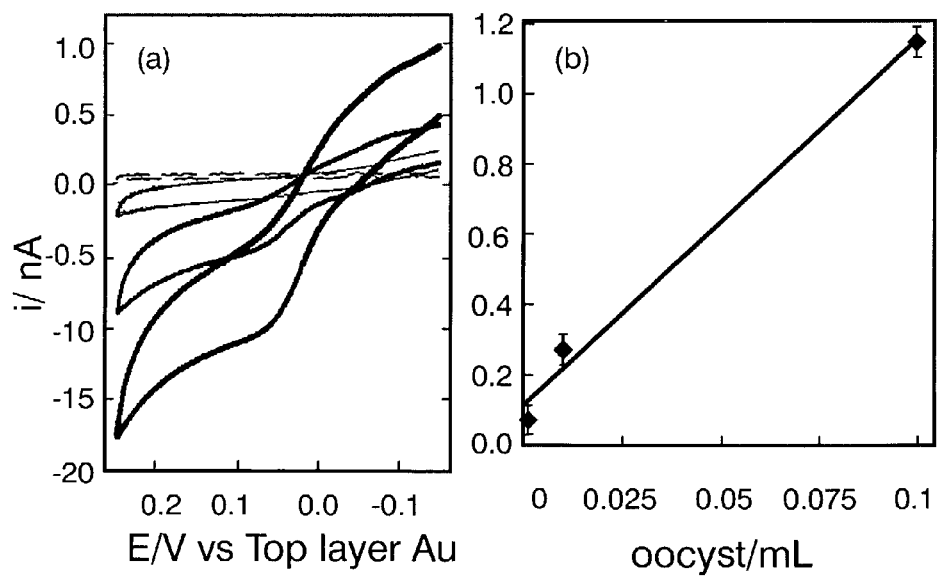
FIG. 7. Dependence of signal for an internal electrochemical setup in a 50-µm cavity on concentration of oocysts immobilized at macrochips using the complete assembly (MUOL SAM+EDC-coupled Ab+Ag+Ab-AP). The TNB of the microcavity served as the working electrode and the top layer of gold served as the pseudoreference/auxiliary electrode. Detection of enzymatically-generated $PAP_R$ took place after the macrochips had soaked in 4 mM PAPP in 0.1 M Tris for 12 h. CV responses (50 mV/s) are shown in (a) for 0 oocysts (dashed curve), 0.001 oocyst/mL (thin solid curve), 0.01 oocyst/mL (medium solid curve), and 0.1 oocyst/ml (thick solid curve). The calibration curve for these concentrations is shown in (b).

The current (average of two measurements) is linear with concentration, giving a least squares fit of y=10.5x×0.1 nA/oocyst/mL, $R^2$=0.991, shown in FIG. 7. A detection limit of $7 \times 10^{-3}$ oocyst/mL or 7 oocysts/L was calculated using equations at the 99%+confidence level (t is ~3 and there are >8 degrees of freedom), where the slope from the calibration curve is 10.4±0.9 nA/oocyst/mL, and the standard deviation from the blank signal with a standard deviation from the blank signal (14 measurements) of $17 \times 10^{-6}$ nA. It must be noted that the oocysts used in these analyses were heat shocked for a total of 20 min at 43-45° C. and the vendor detected 7% ruptured oocysts after the heat shock. Protein fragments of the oocysts walls captured by the immobilized antibody lead to detection of less than one oocyst per mL of sample.

EXAMPLE 3

Immobilization of an Enzyme Linked Immunoassay for Mouse IgG as a Model System on Low Temperature Co-fired Ceramic Tape (LTCC) Material LTCC materials are of interest because they are easily mechanically and chemically machined in the pre-fired state (i.e. soft and pliable "green" tape) and can be layered to make three-dimensional structures for electronics, microelectromechanical, and lab-on-a-chip (including dip-chips) applications. In addition, metallic ink can be screen-printed to pattern electrodes and induce additional functionality. In this example, multi-layered LTCC macrochips are screen-printed with gold ink and modified with self-assembled monolayers (SAMs) of 11-mercapto-1-undecanoic acid and 11-mercapto-1-undecanol. The primary antibody to mouse IgG was covalently attached to the free end of the SAMs using 1-ethyl-3-[3-dimethylaminopropyl] carbodiimide hydrochloride. After capture of the analyte and exposure to a secondary antibody labeled with alkaline phosphatase, the modified LTCC macrochips were incubated in a solution of p-aminophenylphosphate (PAPP), and detection of enzymatically-generated p-aminophenol ($PAP_R$) with cyclic voltammetry was performed by an electrochemical cell that was external to the macrochip. Nonspecific sorption on bare LTCC macrochips was significant, but could be eliminated by sonication or minimized by extended soaking in solution.

Immobilized immunoassays are widely used methodologies for analytical diagnostics. The use of an immobilized antibody provides a simple way of capturing the analyte and separating it from other components of the sample. Commonly used solid substrates include titer plates that are made of polymers, metal electrodes, quartz, magnetic beads, carbon electrodes, films, liposomes, silicon, silica, and glass. Ceramic-based immunoassays with graphite carbon working electrodes have recently also been used. Various substrates have been studied for micrometer dimension biosensor development integrated into microfluidic channels towards the development of micro total analysis systems. The materials now in use include poly(dimethylsiloxane) (PDMS) plastics, silicon, glass, and quartz. Micro total analysis systems (mTAS) are necessary in the miniaturization of bioassays for environmental, biological, industrial, and medical purposes.

The low temperature cofired ceramic (LTCC) tape-based system is one of the most recent platforms for the development of mTAS that are used as three-dimensional conduits integrated with sensing and actuating elements. The LTCC based platform is cheap, easy to fabricate, and can be integrated with conductors and is compatible with fluids to be used in mTAS. The LTCC can be used to construct channels with electrodes within short distances of each other that are individually addressable. The channels permit delivery of small volumes that allows self-contained electrochemical analysis of very small volumes. In this example we show that not only can a heterogeneous immunoassay in such electrochemical systems be applied to small sample volumes, but they also offer competitive, if not better, detection limits, sensitivity, and speed because of the close proximity of electrodes to the immobilizing surfaces. Transferring these devices to closed systems and combining them with microfluidics in mTAS systems further decrease total analysis time.

The material used in this example begins as the "green tape" (pre-fired state). This green tape is soft, pliable, and 112 to 250 mm thick. Structures are easily fabricated in it with a laser, punch, or chemical machining. In its green state, the material consists of alumina and glass frit (silica) particles from 10 to 500 mm, and organic binder. Each layer can be constructed separately, and several can be stacked to form three-dimensional structures with conductors and channels. These layers are laminated and sintered into a hard material as the binder burns out and the glass flows. This hardened material is called the low temperature co-fired ceramic (LTCC).

The ease of manipulation and the inexpensive raw material make LTCC-based platforms a good material for sensor and assay development. Very little work has been done on LTCC in application to electrochemical-based immunoassays. A ceramics-based material has been used to immobilize the components for an immunoassay for rabbit immunoglobulin. Electrochemical detection was performed at neighboring screen-printed carbon ink electrodes. However, the primary antibody was dispersed in the sol-gel mixture before screen-printing onto the ceramic surface. Furthermore, nothing was done to prevent the physisorption of the active components of the immunoassay on the porous ceramic material. In the present invention, the primary antibody is covalently immobilized on gold ink that is screen printed on the ceramic surface. This is a new system and the limitations, irreproducibility, and elimination of the sorption to the bare ceramics is addressed. This makes our invention more adaptable to mTAS and bioassay arrays.

In the present invention, a Au screen printed LTCC platform is used as a substrate for a sandwich type ELISA using mouse IgG. This is the first use of self-assembled monolayers of organothiols for covalent immobilization to the LTCC gold ink. The SAMs are used to attach the primary antibody, Ab, which captures the mouse IgG, the antigen, Ag, from a sample solution. A secondary antibody that is conjugated to alkaline phosphatase, Ab-AP, and attaches to the immobilized Ag and enzymatically generates p-aminophenol ($PAP_R$) from p-aminophenylphosphate (PAPP), which is electrochemically detected by a separate electrode. The present invention is suitable not only for individual chemical sensors or assays on LTCC-based platforms, but also for arrays of sensors and assays. The ceramics can be used for the construction of microfluidic channels for the delivery of small volumes of samples. Therefore, this platform is suitable for high throughput analysis and μTAS chips in biosensor technology that may be automated.

The bare and Au-coated ceramic macrochips (approximately 1.2 cm×2 cm) were made from six layers of the same batch of green tape. The green tape was cut into 6 in$^2$ sheets and then preconditioned at 120° C. for 30 min and allowed to stand for 24 hours. The structures are laid on the green tape including the screen printing of 12 mm thick gold to make the Au-coated ceramic macrochips. It is dried at 120° C. for 5 minutes and inspected for the features with a microscope. Layers were placed one on top of each other before uniaxial lamination in a hydraulic press with heated platens at 70° C. and 3000 psi with 180° rotation every 5 minutes. Cofiring for organic burnout took place between 200° C. to 500° C. The macrochips were diced to size electronically and by hand using a diamond scribe. The chips were rinsed thoroughly with dI water prior to surface modification.

The ceramic macrochips may be cleaned in at least two ways. One is to clean with running DI water and then soaked in DI water for 10 min before use. Another is to clean with piranha for 30 minutes, wash in running DI water thoroughly for 30 minutes then dry with Ar. SAM preparation, rinsing, and drying were carried out completely in an Ar-purged glovebag after the cleaning step to eliminate oxidation of SAMs by air (or ozone). The macrochips were soaked in a 4 mM MUOL in Ar-purged ethanol for 24 h to form SAMs, followed by rinsing with Ar-purged ethanol three times in each of three separate test tubes inside the glovebag. The chips were dried with Ar and kept in closed vials before use.

Covalent immobilization of the primary antibody on the LTCC green tape was performed as described above. Capture of the antigen, mouse IgG and completion of the sandwich type ELISA were also performed as previously described.

The macrochips that were rinsed with 5 mL 0.1 M Tris at pH 9.0 were soaked overnight in 5 mL of enzyme substrate solution of 4 mM PAPP in 0.1 M Tris at pH 9.0.that was purged with Ar (15-30 minutes) and kept from light to minimize oxidation. The enzymatically generated $PAP_R$ was detected using Au as working electrode, Ag/AgCl (saturated KCl) as reference electrode, and Pt flag as counter electrode. Cyclic voltammetry was performed at a potential window of −0.25 to +0.25 V at 50 mVs$^{-1}$.The extent of nonspecific adsorption of active immunoassay components on bare LTCC green tape was studied was substantial.

Pretreatment of the bare ceramic macrochips in attempts to eliminate nonspecific adsorption involved exposing the chips to one of the following solutions overnight: acetate TBSA, 4 mM butanol, 4 mM MOD, 4 mM MOD in acetate TBSA, 20×sodium chloride/sodium citrate buffer (SSC, pH 7.6), and sodium dodecyl sulfate (200 mg/mL). The 4 mM butanol and 4 mM MOD were prepared in ethanol that was purged with Ar. The 4 mM propionic acid solution was prepared with DI water. The bare ceramic macro chips were separately soaked overnight in each of the different solutions. The macro chips dipped in solutions prepared in ethanol solvents were first rinsed three times with 5 mL ethanol. Afterwards, all the chips were rinsed three times in 5 mL DI water before exposure to subsequent solutions.

The activity of the complete assembly on bare ceramic macrochips was evaluated by soaking in PAPP solution. The enzymatically generated $PAP_R$ was detected electrochemically using the same setup used for detection on modified Au coated ceramic macrochips.

Because the nonspecific sorption is due to entrapment of immunocomponents in the crevices of the LTCC material, rather than adsorption, the molecules are given time to naturally diffuse out of the holes. After immunocomponent-modified bare and Au-coated LTCC macrochips were soaked in PAPP solution and electrochemical detection of $PAP_R$ was performed, they were rinsed with continuous flow DI water from a squirt bottle for 5 minutes and soaked in 5 mL acetate TBSA solution for at least 30 min before soaking in a fresh solution of PAPP solution overnight (12 h), followed by CV again. This was repeated over a period of three days. The $PAP_R$ signal was measured daily before soaking in 5 mL acetate TBSA.

After the immunoassay complete assembly modified bare LTCC green tape showed activity, different chips were sonicated for either 1 minute or 2 minutes in 5 mL acetate TBSA solution. After sonication, the chips were places in a test tube with 5 mL acetate TBSA, shaken for 30 seconds and then rinsed with acetate TBSA from a squirt bottle for 5 minutes, before soaking in PAPP solution. Electrochemical results of the activity of the modified surfaces are shown in FIG. 5.7.

Immunoassay activity of modified Au-coated and bare ceramic macrochips was determined by evaluating the surrounding PAPP solution electrochemically for the presence of $PAP_R$. Working electrode (which were either Au-coated silicon wafer or complete assembly-modified Au coated ceramic macrochips) potentials were kept within appropriate ranges (−0.15 to 0.25 V) to avoid electrochemical conversion of PAPP into $PAP_R$. Modified Au-coated ceramics chips were rinsed with DI water and dried with N2 before use as working electrode in an external setup.

Bare LTCC (b), double sided (ds) Au screen-printed LTCC (c), and the single sided (ss) ASu screen-printed LTCC (d) surface exhibit irregularly shaped crevices or holes with sizes ranging from ~1 to >2 mm in width. Most of the holes or crevices are smaller than those in alumina that is a component of the green tape before it is cofired. These crevices may be a disadvantage in that they will trap assay components in an active conformation and contribute to the immunoactivity.

Activity of LTCC macrochip surfaces that were exposed to the immunocomponents was investigated by detecting the enzymatically-generated $PAP_R$, from a PAPP solution in which the macrochips had soaked for 12 h, at a nearby bare Au coated silicon wafer working electrode. The current obtained with MUA-SAMs plus complete assembly were consistently lower by 13% than when MUOL SAMs were used. We have observed a similar trend with the mouse IgG assay using Au-coated silicon wafer chips. Because a larger response is obtained with MUOL, we focus on these kinds of SAMs. As expected, the double-sided Au-coated macrochips yield an increased assay signal, compared to the single-sided ones. However, the increase is not twice that of the single sided Au-coated macrochips. This is due to nonspecific sorption on the bare side, making the signal at the ss Au unusually high.

To determine the extent of nonspecific sorption or adsorption to bare LTCC macrochips, they were subjected to the same surface modification processes as the Au-coated LTCC macrochips, and enzymatically generated $PAP_R$ was detected. FIG. 5.4 shows the electrochemical results for both complete and incomplete immunoassay assemblies. The complete assembly with and without SAMs exhibited significant generation of $PAP_R$, thereby, indicating that the immunoassay components physiosorb and/or are trapped within the crevices in an active form. The incomplete assemblies containing AP~Ab also exhibited immunoactivity. The incomplete assemblies always gave a lower signal than the complete assembly that may be attributed to dislodging the physisorbed material in the crevices during the washing steps. Surprisingly, the electrochemical signal for the assay on the bare LTCC macrochips is anywhere from 50% to 200% higher than that for ds Au LTCC macrochips. Another surprising result is that given the high immunoactivity of the bare LTCC macrochips one might expect that the ss Au-coated LTCC macrochips would provide more activity than the ds Au-coated chips. It is possible that the Au coating fills up some of the crevices decreasing the amount of space available for physisorption for the Ab~AP which is a big molecule. Physisorption of the immunoassay components on silicon dioxide coated silicon wafers have not been previously observed. A smooth surface like those of a silicon wafer surface does not have spaces that can entrap the immunoassay components unlike the LTCC green tape surface that is rough. Several strategies were investigated to eliminate the activity due to sorption on the bare LTCC material. They are based on pretreatments that we tested for passivating polyimide in previous studies. One unsuccessful approach involved first exposing the macrochips to acetate TBSA solution in order to block possible protein adsorption sites before proceeding with the immunoassay assembly. Other pretreatments did not prevent sorption either. Extended soaking in the acetate TBSA washing buffer was tested to eliminate the physisorption. The signal from enzymatically-generated $PAP_R$ decreases with increasing soaking time in solution. This shows that the entrapped molecules are slowly diffusing out of the crevices on the rough LTCC surface rather than a loss in the activity of the immunoassay components because our previous experiments with the complete assembly modified Au-coated silicon wafer macrochips did not lose activity even after 4 months of soaking in acetate TBSA solution. Even after four days, the bare LTCC chips still exhibited immunoactivity. The soaking method is not efficient and does not complete the job.

Figure 8:
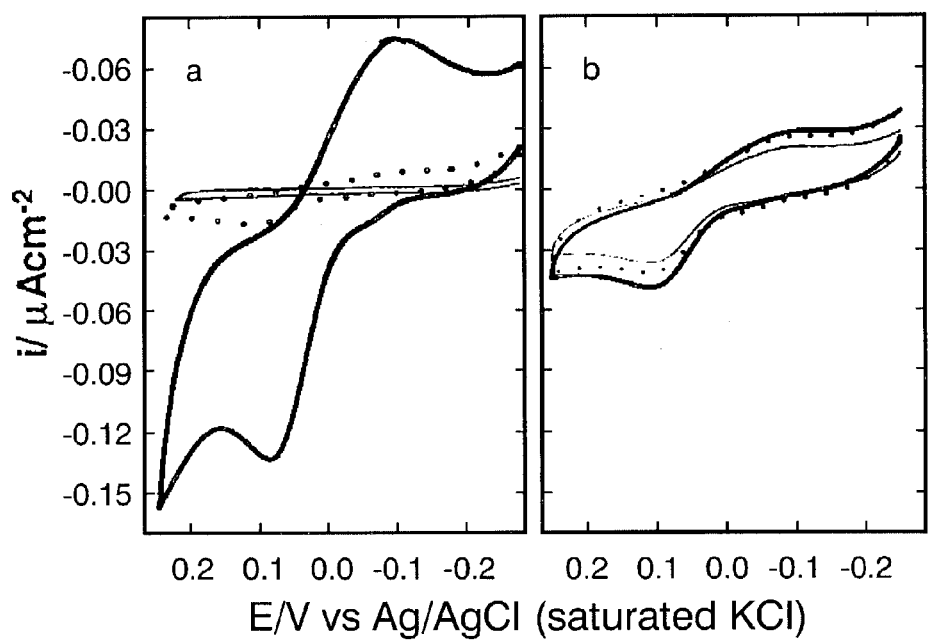
FIG. 8. Effect of sonication in removing non-specifically sorbed species from LTCC macrochips (plain (a) and ss Au (b)) that had been modified with the complete assembly (SAM=MUOL). Macrochips were either not sonicated (solid curve) or sonicated in 5 mL acetate TBSA solution for 1 min (dotted curve) or 2 min (thin solid curve) before soaking in PAPP solution. Conditions and CV parameters are the same as those in FIG. 3.

Modified ss Au-coated and bare LTCC macrochips were sonicated for different times in acetate TBSA solution before soaking in PAPP solution. After 2 min of sonication, the bare LTCC chips no longer exhibited immunoactivity, presumably because entrapped molecules were dislodged from the crevices and freed (FIG. 8). Thus, it is assumed that the signal achieved after sonicating for 2 min is the signal for specifically-adsorbed species to the gold. Au-coated LTCC chips with the complete assembly that were sonicated for 2 min only lost 13.3% activity that may be attributed partly to loss of physisorption to the sides of the chip that were not coated with gold and to some loss in activity that maybe due to denaturation of proteins. However, the loss in activity resulting in denaturation is very minimal compared with the loss due to release of the entrapped molecules because the percentage loss in activity on the bare LTCC surface is almost 100%. A typical signal from a Au-coated silicon wafer macrochip of the same size as the LTCC chip modified with the mouse IgG immunoassay in exactly the same way, gives a signal of 27.7 $Acm^{-2}$ while that of the non-sonicated Au-coated LTCC is 34.6 $Acm^{-2}$. After 2 min of sonication, the LTCC signal, 30 $Acm^{-2}$, is still higher than the signal from the Au-coated silicon wafer that indicates that not all the entrapped immunoassay components were dislodged by the sonication process.

Bare and modified Au-coated LTCC chips can be used as working electrodes. This is useful in an electrochemical immunoassay with minimized number of electrodes that can be used in miniaturized devices for small volume analysis. Au-coated LTCC surfaces, both bare and modified with the MUOL SAMs and the complete assembly, were used as working electrodes in a solution of 4 mM $PAP_R$ in 0.1 M Tris, pH 9.0. The peak splitting is large (100 mV Ep) at the Au-coated silicon wafer. Ideal peak splitting for a reversible, two-electron transfer is 30 mV. The nonideality is due to the quasireversible kinetics. Bare Au-coated LTCC electrodes exhibit higher resistance (Ep=500 mV for ss Au and 600 mV for ds Au), which could be due to the nature of the gold ink or due to poor connection to the gold via the alligator clips that connect to the leads of the potentiostat. If we account for a higher resistance, the electrochemical signal of the ss Au-coated LTCC working electrode is about the same as that of the ss Au-coated silicon wafer chip, which would be expected if the diffusion layers from the rough features overlap, exhibiting an overall planar diffusive behavior. The ds Au-coated LTCC working electrode has a peak current that is more than 3 times larger than that of the ss Au-coated LTCC chip. The Ep is larger presumably due to the larger current, and therefore a higher iRu drop occurs. Au-coated LTCC chips modified with SAMs and the complete assembly, show a significant current, and therefore can be used to detect PAP. As expected, the signal at the modified ds Au-coated LTCC is larger than that at the modified chip that is only coated on one side with Au, although it is less than twice. Modified Au-coated silicon wafer chips are completely passivated when modified with the complete assembly. Unlike the passivation of the smooth Au-coated silicon wafer that rendered these to be non-usable as detecting electrodes for PAP, the rough surface of the modified Au-coated LTCC still has Au-surfaces that were not completely modified. These non-modified sections or bare spots on the rough surface allowed penetration of the PAP for detection. The ss modified gold LTCC shows a bigger signal than the ss bare gold LTCC while ds Au-coated LTCC chip has a signal that is less than twice that of the ss Au for modified and bare electrodes. All these observations may be attributed to possible non-uniformity of the LTCC surface that led to the non-uniformity in the gold-screen printing.

The success of immunoassays on a ceramics-based platform is a new concept that provides new possibilities in bioassay development. We have demonstrated the utility of the features of this device in an electrochemical immunoassay with mouse IgG as the analyte.

LTCC materials are used for three dimensional structures but the use in mTAS and LOCS in bioassays is new. We have developed LTCC chip-based immunoasay for mouse IgG that involves covalent immobilization of the primary antibody. We have also solved the problem of nonspecific sorption on the LTCC. This is important for bioassay platforms for reproducible responses, and for use in arrays of structures.

Whereas, the present invention has been described in relation to the drawings attached hereto, it should be understood that other and further modifications, apart from those shown or suggested herein, may be made within the spirit and scope of this invention.

What is claimed is:

1. A method for analyzing at least one microorganism in a solution, comprising the steps of:

heat shocking said microorganism causing said microorganism to release heat shock polynucleotides;

allowing said heat shock polynucleotides to transfer to a self-contained microassay structure having at least one integrated, individually addressable electrode and an assay surface, wherein said at least one integrated, individually addressable electrode is a detecting electrode constructed adjacent to or within a diffusion layer of said assay surface, said assay surface having a primary polynucleotide probe complementary to a portion of said heat shock polynucleotides;

addition of a secondary polynucleotide probe complementary to a portion of said heat shock polynucleotides and having an electroactive complex covalently attached, wherein said electroactive complex may be activated such that an electric current is generated within said microassay structure, and wherein said electroactive complex does not transfer electrons directly to said detecting electrode for generation of said electric current;

allowing said secondary polynucleotide probe and said electroactive complex to bind to said heat shock polynucleotides;

activating said electroactive complex attached to said secondary polynucleotide probe;

measuring said electric current generated by said activation of said electroactive complex at said detecting electrode.

2. The method of claim 1 further comprising applying a polymerase chain reaction subsequent to said heat shocking of said microorganism.

3. The method of claim 1 wherein said at least one integrated, individually addressable electrode of said microassay structure further comprises a solid capture electrode integrated on a solid substrate, an additional detecting electrode, and an auxiliary electrode.

4. The method of claim 3 wherein said solid substrate is fabricated using ceramic tape.

5. The method of claim 1 wherein said microassay structure is comprised of low temperature co-fired ceramic tape and metallic ink.

6. The method of claim 5 wherein said ceramic tapes serves as a substrate for said at least one integrated, individually addressable electrode.

7. The method of claim 1 wherein said microassay structure is comprised of a dip-chip and/or a microcavity array chip, said chip being integrated with at least one individually addressable electrode.

8. The method of claim 1 wherein said activating said electroactive complex is selected from the group consisting of changing temperature, changing pH, application of electrical currents, exposure to electromagnetic radiation, denaturation and addition of an activating compound.

9. The method of claim 1 wherein said at least one microassay structure is comprised of a plurality of microassay structures.

10. The method of claim 1 wherein said analyte is a bacteria, protozoa, or other microorganism.

11. The method of claim 1 wherein said at least one microorganism is selected from the group consisting of *Cryptosporidium parvum*, *Escherichia coli*, *Campylobacter lari*, *Giardia lamblia*, *Listeria monocytogenes*, *Bacillus anthracis*, *Plasmodium* species, *Staphylococcus* species and *Salmonella typhi*.

12. The method of claim 1 wherein said electroactive complex is selected from the group consisting of a metalloprotein, a synthetic dendrimer, a redox enzyme, a chelating agent, an enzyme, a polymer and an inorganic species.

13. The method of claim 1 wherein said microassay structure is formed by photolithographic means.

14. The method of claim 1 wherein said microassay structure is formed by photolithographic means on ceramic tape, polymeric materials, silicon wafer, or glass.

15. The method of claim 1 wherein said at least one integrated, individually addressable electrode is fabricated using ceramic tape.

16. The method of claim 1 wherein said secondary polynucleotide probe does not include nanoparticle labels attached to oligonucleotides.

17. The method of claim 1 wherein said transferring said heat shock polynucleotides includes allowing said heat shock polynucleotides to diffuse into said second microassay structure.

18. A method for analyzing at least one microorganism in a solution, comprising the steps of:

heat shocking said microorganism causing said microorganism to release heat shock polynucleotides;

allowing said heat shock polynucleotides to transfer to a self-contained microassay structure having at least one integrated, individually addressable electrode and an assay surface, wherein said at least one integrated, individually addressable electrode is a detecting electrode constructed adjacent to or within a diffusion layer of said assay surface, said assay surface having a primary polynucleotide probe complementary to a portion of said heat shock polynucleotides;

addition of a secondary polynucleotide probe complementary to a portion of said heat shock polynucleotides and having an electroactive complex covalently attached, wherein said electroactive complex may be activated such that an electric current is generated within said microassay structure, and wherein said electroactive complex does not transfer electrons directly to said detecting electrode for generation of said electric current;

allowing said secondary polynucleotide probe and said electroactive complex to bind to said heat shock polynucleotides;

activating said electroactive complex attached to said secondary polynucleotide probe;

measuring said electric current generated by said activation of said electroactive complex at said detecting electrode; and wherein said microorganism is selected from the group consisting of *Cryptosporidium parvum*, *Escherichia coli*, *Campylobacter lari*, *Giardia lamblia*, *Listeria monocytogenes*, *Bacillus anthracis*, *Plasmodium* species, *Staphylococcus* species and *Salmonella typhi*.

* * * * *